(12) United States Patent
Redmond et al.

(10) Patent No.: US 11,877,775 B1
(45) Date of Patent: Jan. 23, 2024

(54) MULTIAXIAL RECEIVERS WITH TETHER

(71) Applicant: Warsaw Orthopedic, Inc., Warsaw, IN (US)

(72) Inventors: Jerald Redmond, Germantown, TN (US); Stan Palmatier, Ramer, TN (US); Caleb Smith, Collierville, TN (US); Larry McBride, Germantown, TN (US); Dimitri Protopsaltis, Memphis, TN (US); Mike Sherman, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 18/057,496

(22) Filed: Nov. 21, 2022

(51) Int. Cl.
*A61B 17/70* (2006.01)
(52) U.S. Cl.
CPC .................. *A61B 17/7032* (2013.01)
(58) Field of Classification Search
CPC ............ A61B 17/7019; A61B 17/7022; A61B 17/7026–7031; A61B 17/7049–7053
See application file for complete search history.

(56) References Cited

U.S. PATENT DOCUMENTS

| | | | |
|---|---|---|---|
| 5,180,393 A | 1/1993 | Commarmond | |
| 5,425,767 A | 6/1995 | Steininger et al. | |
| 6,576,017 B2 | 6/2003 | Foley et al. | |
| 7,942,902 B2 | 5/2011 | Scwab | |
| 8,034,083 B2 | 10/2011 | Abdelgany et al. | |
| 8,070,785 B2 | 12/2011 | Biscup | |
| 9,039,708 B2 | 5/2015 | Arroque-Lahitette | |
| 9,113,966 B2 | 8/2015 | Baccelli et al. | |
| 9,144,440 B2 | 9/2015 | Aminian | |
| 9,770,268 B2 | 9/2017 | Albert et al. | |
| 10,568,674 B1 | 2/2020 | Eichenseer | |
| 10,595,904 B2 | 3/2020 | Albert et al. | |
| 10,758,274 B1 * | 9/2020 | Bess | A61B 17/7023 |
| 11,026,722 B2 | 6/2021 | Albert et al. | |
| 11,185,353 B2 | 11/2021 | Prygoski et al. | |
| 11,207,107 B2 | 12/2021 | Mickiewicz et al. | |
| 11,246,630 B2 | 2/2022 | Akbarnia et al. | |
| 2004/0254574 A1 * | 12/2004 | Morrison | A61B 17/7037 606/301 |

(Continued)

FOREIGN PATENT DOCUMENTS

WO 2016166448 A1 10/2016

*Primary Examiner* — Eduardo C Robert
*Assistant Examiner* — Michelle C Eckman
(74) *Attorney, Agent, or Firm* — FOX ROTHSCHILD LLP

(57) ABSTRACT

A multiaxial receiver may include a body having a U-shaped cavity configured to receive a longitudinal rod therein and a lower cavity configured to couple to a pedicle screw. The multiaxial receiver may include a first passageway configured to permit a tether to pass therethrough in the vertical direction. In some embodiments, the multiaxial receiver may also include a second passageway configured to permit a tether to pass therethrough in the horizontal direction. An immobilization assembly including a set screw and a wedge may immobilize the tether. The immobilization assembly may be configured to be rotated from an open position in which the tether is permitted to pass through the first passageway to a closed position in which the tether is immobilized within the first passageway or second passageway by pining the tether against a bearing surface of the first passageway.

18 Claims, 25 Drawing Sheets

(56) References Cited

U.S. PATENT DOCUMENTS

| | | | |
|---|---|---|---|
| 2014/0094850 A1* | 4/2014 | Clement | A61B 17/7053 |
| | | | 606/263 |
| 2014/0257397 A1* | 9/2014 | Akbarnia | A61B 17/7053 |
| | | | 606/279 |
| 2016/0235447 A1* | 8/2016 | Mundis, Jr. | A61B 17/7037 |
| 2018/0078286 A1 | 3/2018 | Le Couedic | |
| 2018/0132905 A1* | 5/2018 | Le Couëdic | A61B 17/7053 |
| 2021/0145486 A1 | 5/2021 | Mosnier et al. | |
| 2021/0322059 A1 | 10/2021 | Eichenseer | |
| 2022/0104853 A1* | 4/2022 | Murray | A61B 17/7053 |
| 2022/0151662 A1 | 5/2022 | Murray | |

* cited by examiner

97D

300

MULTIAXIAL RECEIVERS WITH TETHER

FIELD

The present technology is generally related to implants that may be used in spinal fixation surgery. More particularly, the disclosure herein may be directed to implants and implant systems having apertures for passing of a tether, ligature, and/or artificial ligament tape to further stabilize and support the implant and patient anatomy. Disclosed implants may be multiaxial receivers that may pop on to a bone screw or a pedicle screw. Additionally, various implants may have at least one aperture for passing of a tether therethrough and an immobilization means to secure the tether to the implant.

BACKGROUND

There are a variety of structures and methods for treating one or more degenerated, deformed or damaged vertebral stages of a patient's spinal column by means of internal spinal fixation. Typically, this involves the attachment of a spinal implant system to provide a construct that is attached to two or more adjacent vertebrae to support and stabilize the vertebrae in order to allow them to fuse together in a stationary relationship relative to each other. Spinal fusion constructs typically include pedicle screws and longitudinal support members or rods that are attached to the pedicle screws and together they may fix the position of the adjacent vertebrae to which they are attached.

The related art teaches various anchoring devices that are attached to a construct and allow the surgeon to fasten a tether and/or ligament tape to the construct. However, these specialized anchoring devices result in a construct that adds them as one or more additional devices that must be included in the construct. The additional devices increase the space occupied by the construct, require additional manipulation by the surgeon, and must be taken into account. Additionally, these constructs are typically uniaxial, have a relatively high height, and therefore do not provide adequate adjustability for a surgeon.

The term "tether" is used in a generic sense to refer to a type of cordage that is available for surgeons to perform various procedures for use with disclosed implant embodiments. The related art may refer to equivalent structures as tape, cable, rope, ligature, wire, braid, band, or strand. Typically, these structures may be elongated structures that are flexible so that they bend easily (with the application of relatively little force) but also have a strong resistance to being stretched longitudinally by a substantial pulling force. For example, these structures have a relatively high tensile strength and relatively low compressive strength.

SUMMARY

This disclosure generally relates to multiaxial receivers for performing a surgery to a spinal column of a patient. Various multiaxial receivers may have at least one aperture for receiving a tether therein and the tether may be wrapped around pedicle portions of a vertebrae to further stabilize the patients spinal column.

In one aspect, the present disclosure provides for a multiaxial receiver. In various embodiments the multiaxial receiver may include a body having a U-shaped cavity configured to receive a longitudinal rod therein and a lower cavity configured to couple to a pedicle screw. The body may extend in a vertical direction along a longitudinal axis and extending horizontally along a widthwise axis. The multiaxial receiver may include a side portion including a first aperture on an upper surface thereof and a second aperture on a bottom surface thereof, and the first and second apertures may together define a first passageway configured to permit a tether to pass therethrough in the vertical direction. The multiaxial receiver may include a threaded aperture extending through the upper surface and into the first passageway, and an immobilization assembly including a set screw and a wedge. The set screw may be disposed within the threaded aperture. In at least some embodiments, the immobilization assembly may be configured to be rotated from an open position in which the tether is permitted to pass through the first passageway to a closed position in which the tether is immobilized within the first passageway. In some embodiments, in the closed position, the wedge may be configured to pin the tether against a bearing surface of the first passageway.

In another aspect, a multiaxial receiver includes a body having a U-shaped cavity configured to receive a longitudinal rod therein and a lower cavity configured to couple to a pedicle screw. In various embodiments, the body may extend in a vertical direction along a longitudinal axis and extend horizontally along a widthwise axis. In various embodiments a side portion may include a first aperture extending through a side surface thereof that defines a first passageway configured to permit a tether to pass therethrough in the horizontal direction. In various embodiments, a threaded aperture may extend through the upper surface and into the first passageway, and an immobilization assembly including a set screw and a wedge may be disposed within the threaded aperture. In various embodiments, the immobilization assembly is configured to be rotated from an open position in which the tether is permitted to pass through the first passageway to a closed position in which the tether is immobilized within the first passageway. In various embodiments, in the closed position, the wedge is configured to pin the tether against a bearing surface of the first passageway.

In another aspect, multiaxial receiver including a body having a U-shaped cavity configured to receive a longitudinal rod therein and a lower cavity configured to couple to a head of a pedicle screw that permits multiaxial orientation of the body with respect to an extension direction of the pedicle screw is disclosed. In various embodiments, the body may extend in a vertical direction along a longitudinal axis and extending horizontally along a widthwise axis. In various embodiments, the multiaxial receiver may include a side portion including a first passageway configured to permit a tether to pass therethrough in the horizontal direction and a second passageway configured to permit the tether to pass therethrough in the vertical direction. In various embodiments, a threaded aperture may extend through the upper surface and into a common space of the first passageway and the second passageway. In various embodiments, an immobilization assembly may include a set screw and a wedge, and the set screw may be disposed within the threaded aperture. In various embodiments, the immobilization assembly may be configured to be rotated from an open position in which the tether is permitted to pass through the first passageway to a closed position in which the tether is immobilized within the common space, and in the closed position, the wedge may be configured to pin the tether against a bearing surface of the common space.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
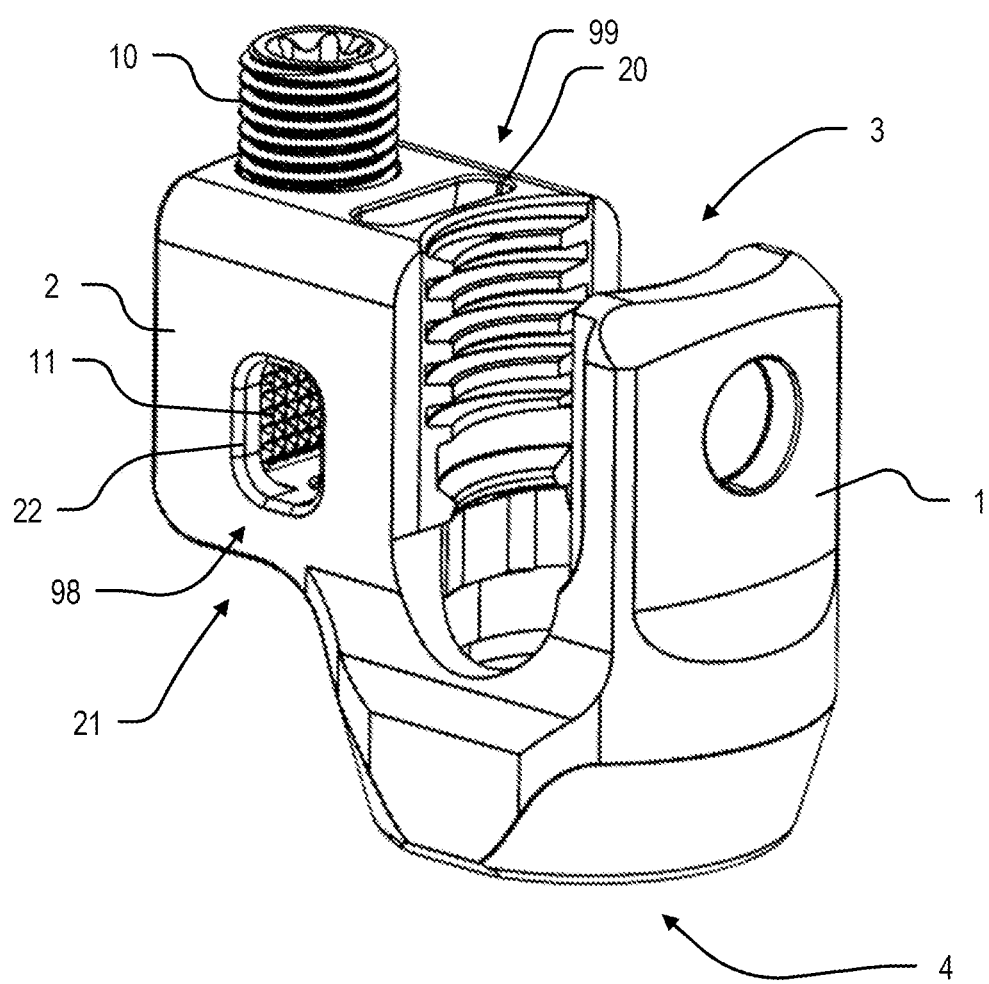
FIG. 1 is a perspective view of a first multiaxial receiver embodiment.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-25 generally, various multiaxial receivers 100, 101, 102, 200, 300 for use with a tether are disclosed. The components can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe, polylactic acid or polylactide and their combinations.

Figure 2:
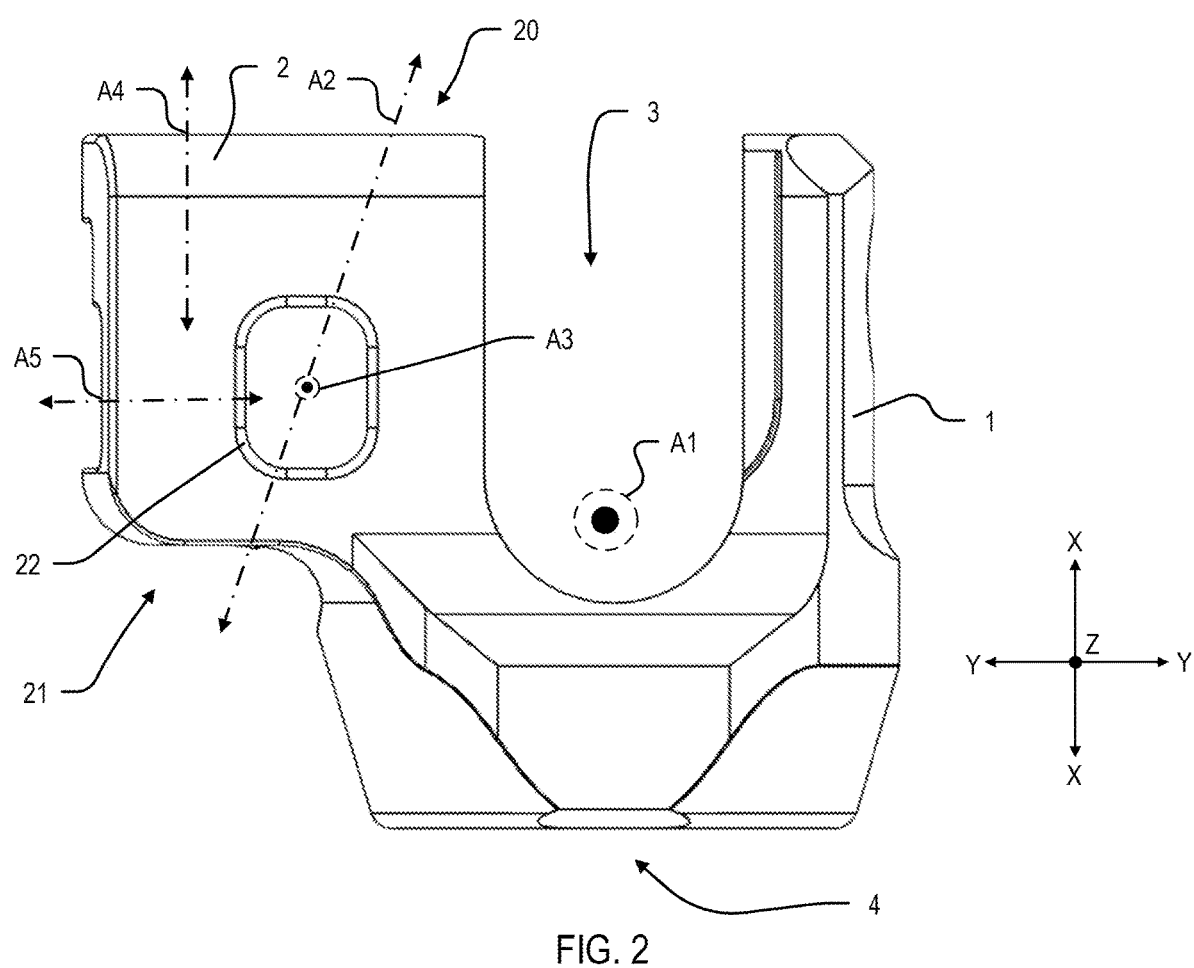
FIG. 2 is a front view of the first multiaxial receiver embodiment of FIG. 1.
Figure 3:
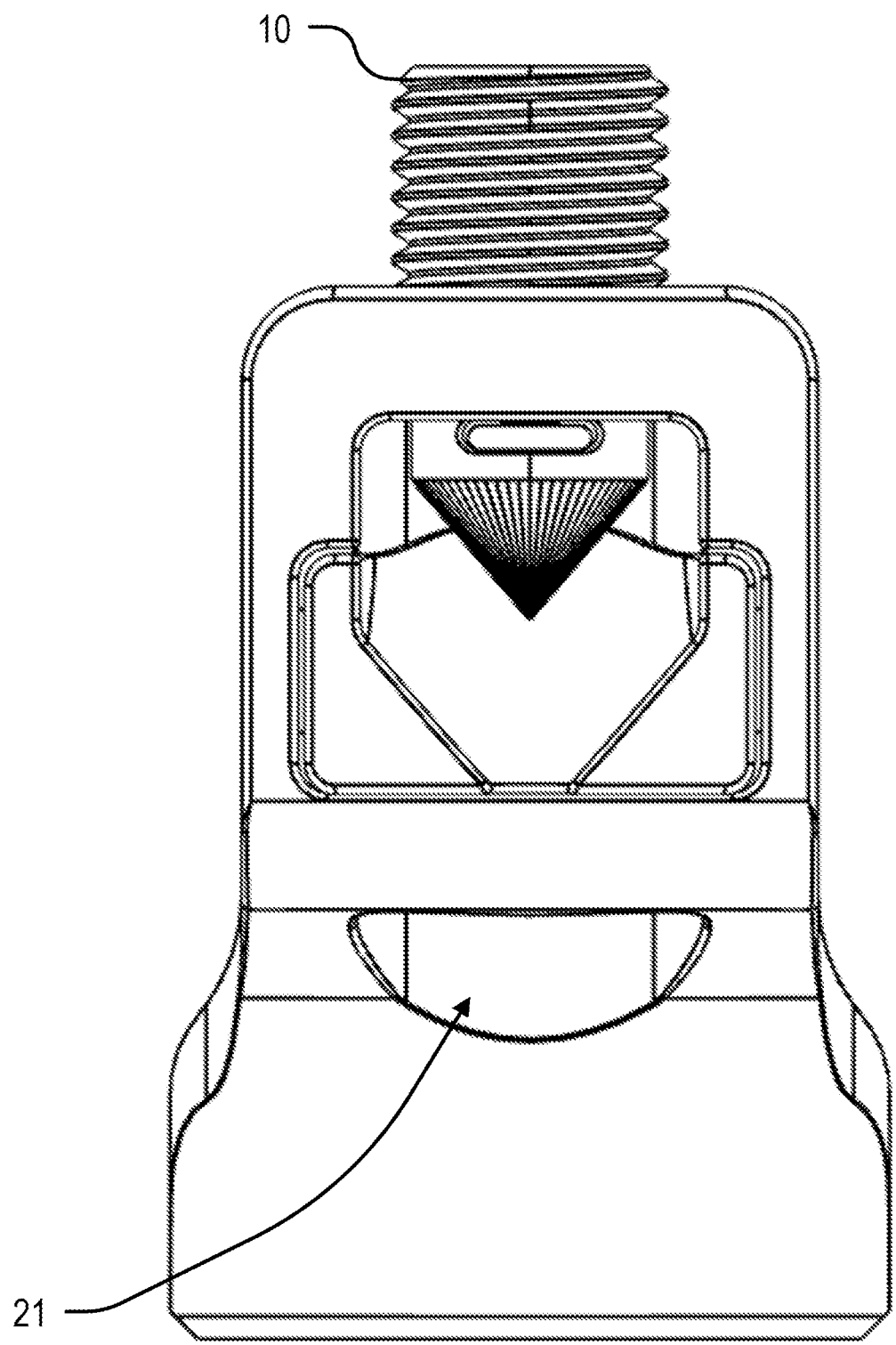
FIG. 3 is a side view of the first multiaxial receiver embodiment of FIG. 1.
Figure 4:
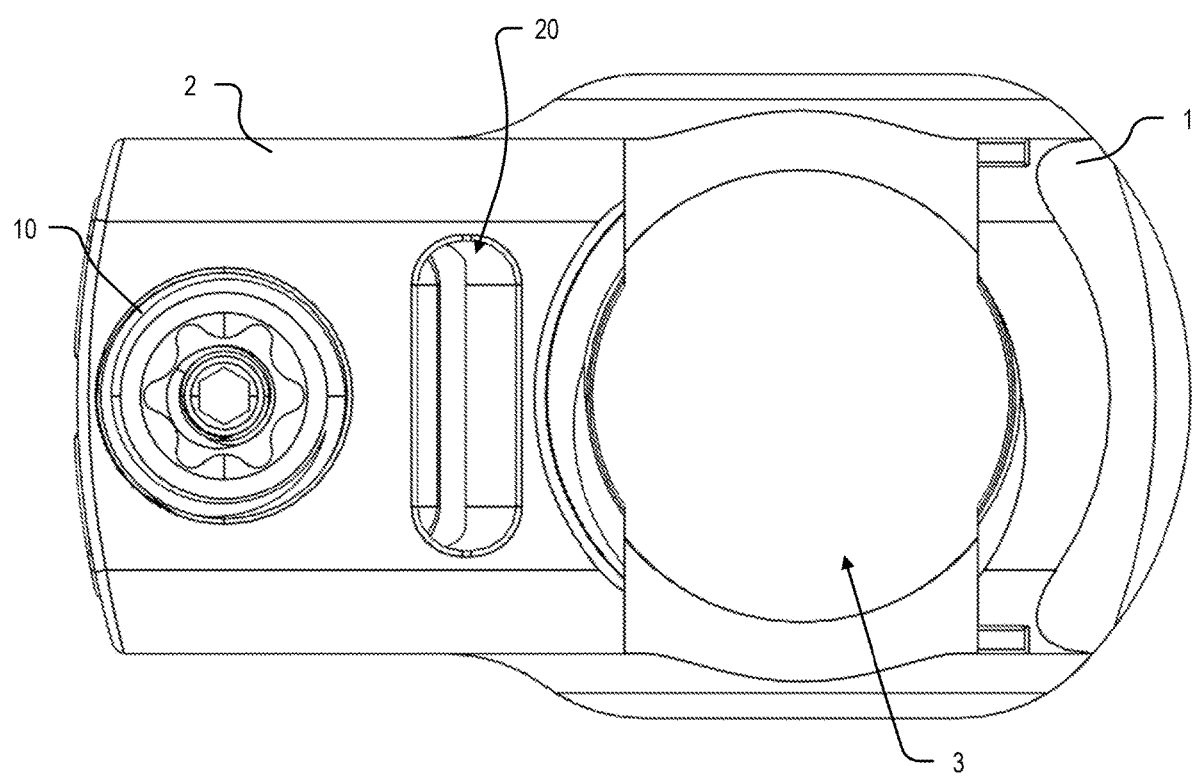
FIG. 4 is a top view of the first multiaxial receiver embodiment of FIG. 1.
Figure 5:
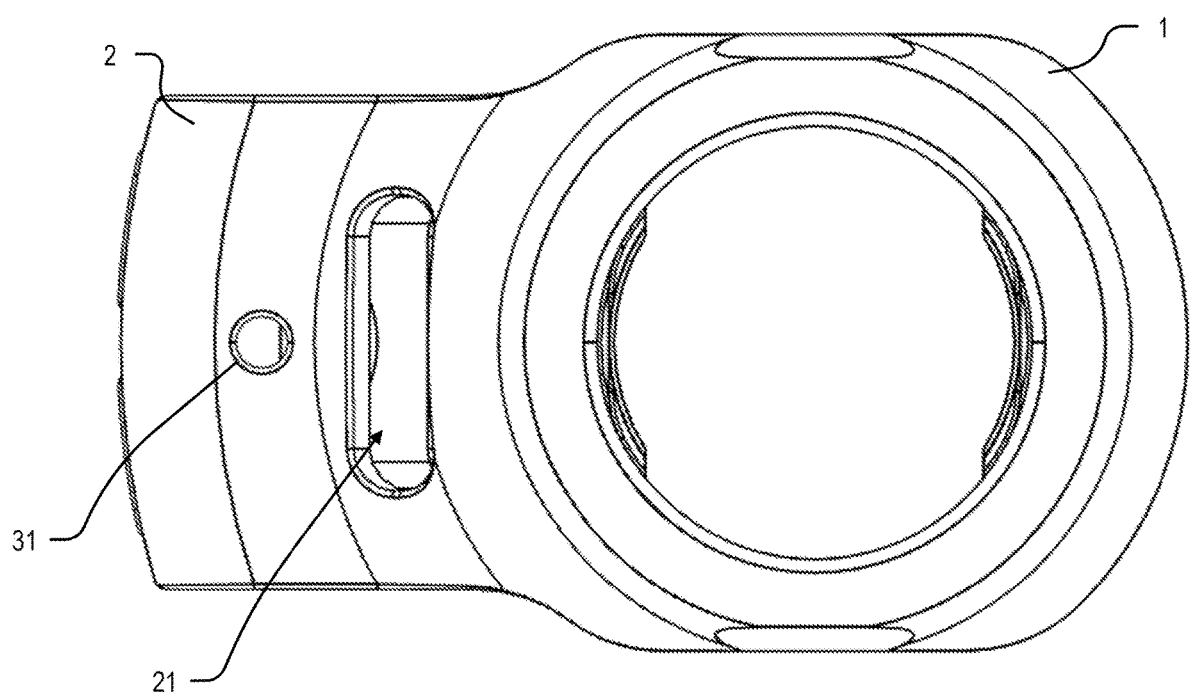
FIG. 5 is a bottom view of the first multiaxial receiver embodiment of FIG. 1.
Figure 6:
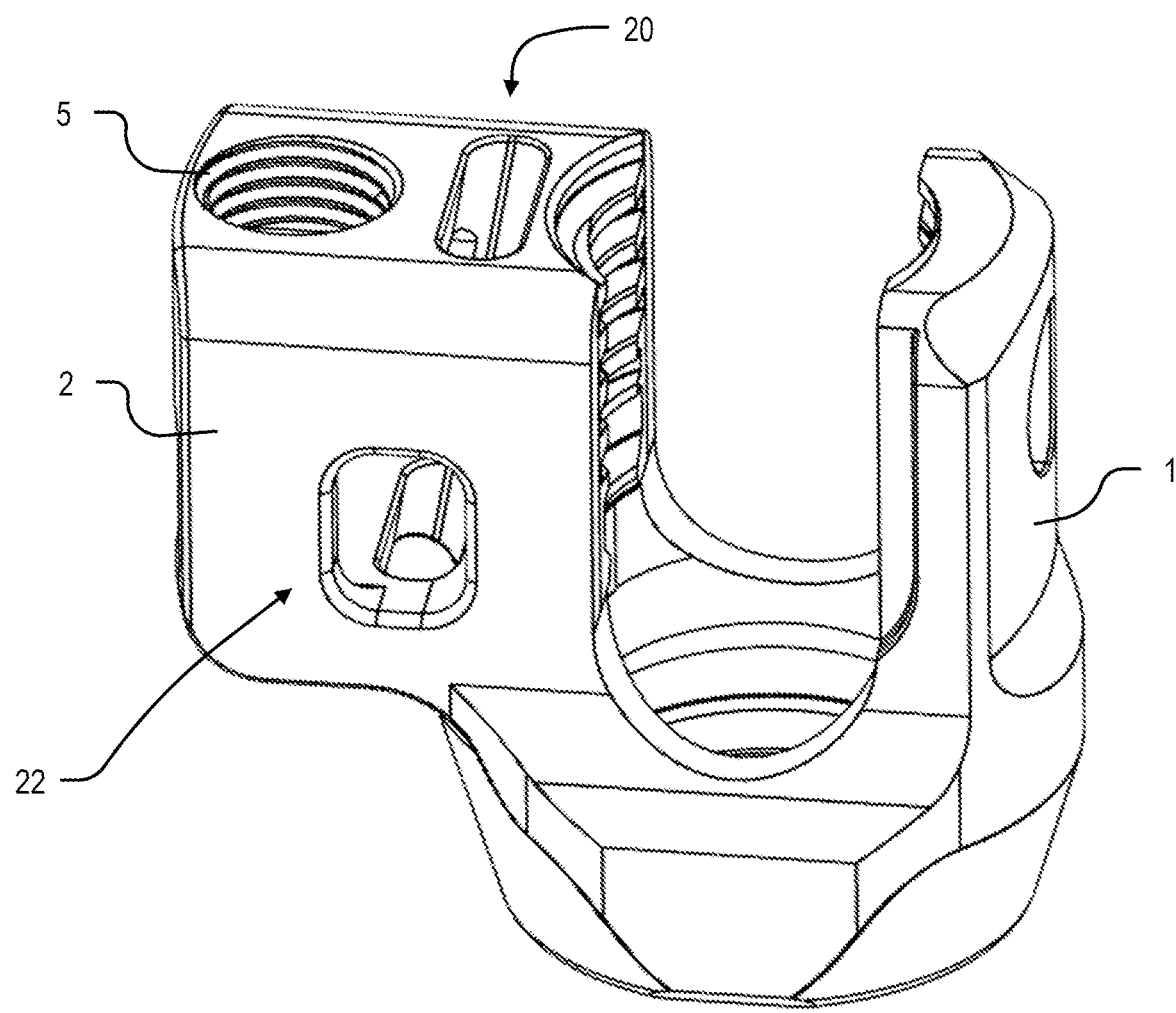
FIG. 6 is a partial parts perspective view of the first multiaxial receiver embodiment of FIG. 1.
Figure 7:
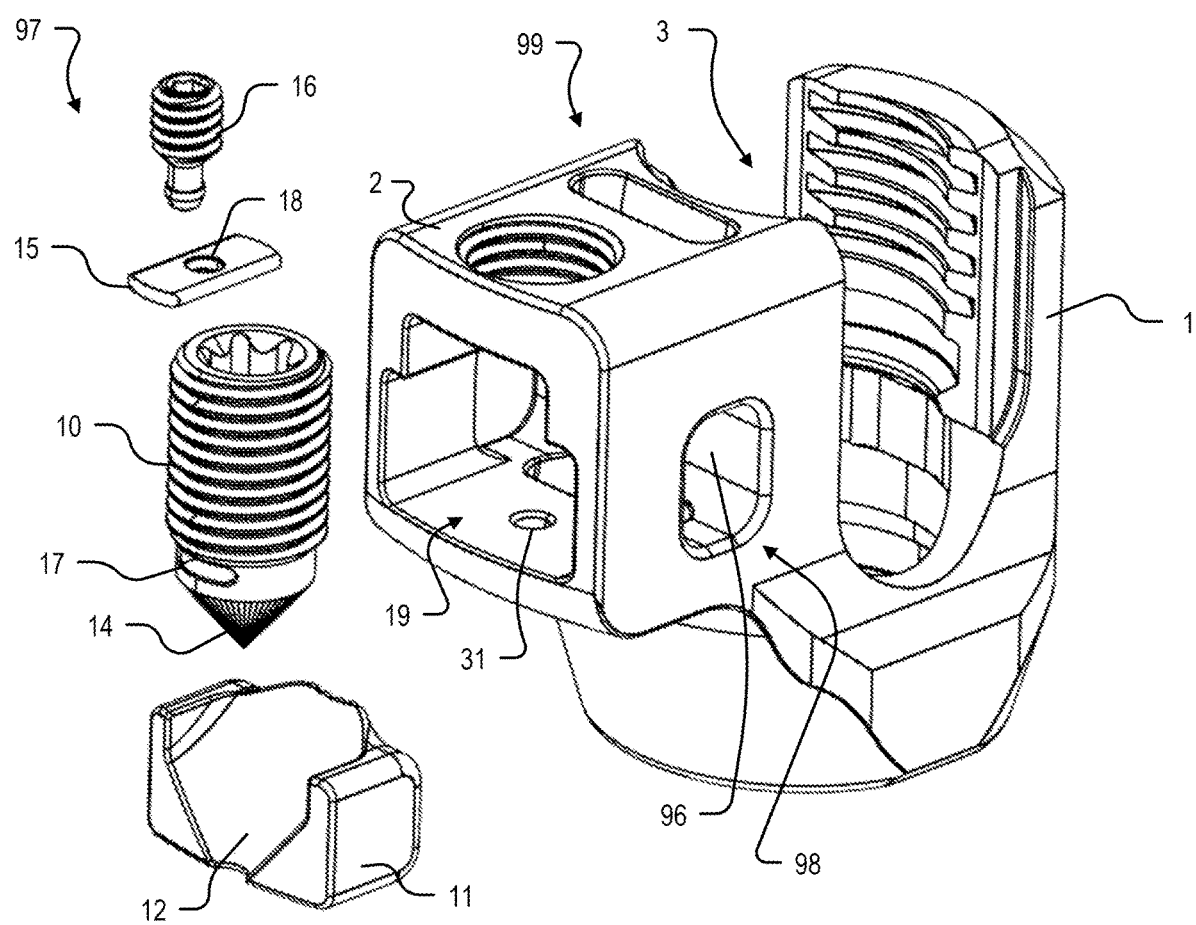
FIG. 7 is an exploded parts view of the first multiaxial receiver embodiment of FIG. 1.
Figure 8A:
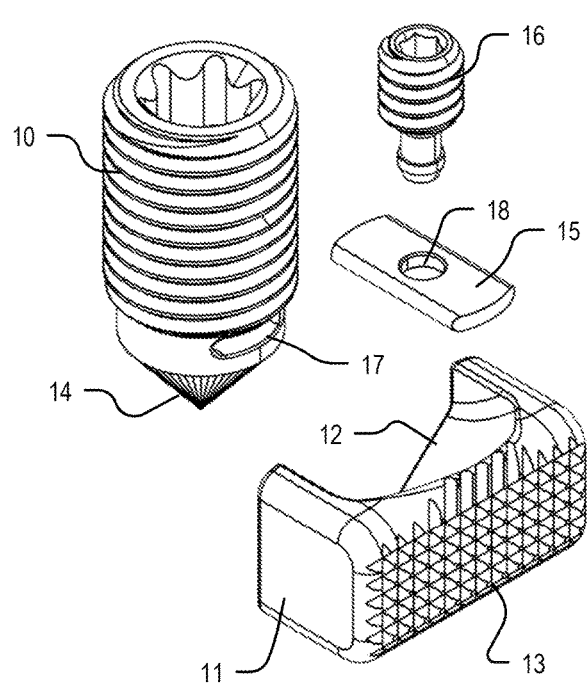
FIG. 8A is an exploded parts view of a first immobilization assembly.
Figure 8B:
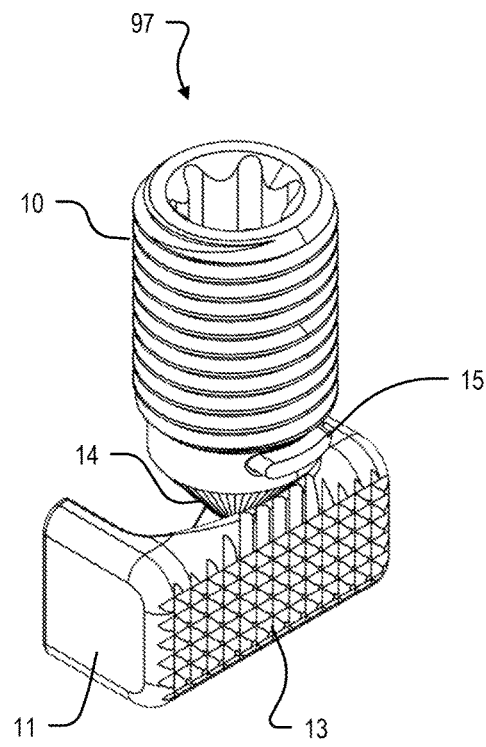
FIG. 8B is an assembled parts view of the immobilization assembly of FIG. 8A.

FIGS. 1-8B illustrate a first embodiment of a multiaxial receiver 100. FIG. 1 is an assembled perspective view, FIG. 2 is a front view, FIG. 3 is a side view, FIG. 4 is a top-down view, FIG. 5 is a bottom-up view, FIG. 6 is a partial parts perspective view, FIG. 7 is an exploded parts view, FIG. 8A is an exploded parts view of an immobilization assembly, and FIG. 8B is an assembled parts view of the immobilization assembly of FIG. 8A.

Referring generally to FIGS. 1-8B, receiver 100 may include a body 1 having a lower cavity 4 for coupling with the head of a pedicle screw (not illustrated) and a U-shaped rod receiving cavity 3 for receiving a longitudinal rod therein (not illustrated). In various embodiments, the body 1 may extend in a vertical direction along a longitudinal axis and extend in a horizontal direction along a widthwise axis. In various embodiments, the longitudinal rod may be oriented in a horizontal direction along Axis A1 (see FIG. 2). In various embodiments, the lower cavity 4 may include slots for housing various rings, crowns, c-clips etc. that allow receiver 100 to couple to the head of a pedicle screw in a multitude of angled orientations, i.e., receiver 100 may be a multiaxial receiver as understood by a person of ordinary skill in the art. In the example embodiment, the U-shaped cavity may include a thread form for mating with a set screw that secures the longitudinal rod from above as understood by a person of ordinary skill in the art.

Body 1 may include an enlarged side portion 2 with various apertures and passageways for receiving a tether (not illustrated) and various types of immobilization assemblies for securing the tether with respect to the receiver 100. In this embodiment, receiver 100 may include a vertical tether receiving passageway 99 defined by a first aperture 20 extending through an upper surface of side portion 2 (see FIGS. 1 and 4) and a second aperture 21 extending through a lower surface of side portion 2 (see FIGS. 3 and 5). With reference to FIG. 2, the vertical tether receiving passageway 99 may define a second axis A2. Additionally, receiver 100 may include a horizontal tether receiving passageway 98 defined by third aperture 22. For example, third aperture 22 may extend through the enlarged side portion 2 from a first sidewall surface to a second sidewall surface opposite the first sidewall surface. As seen best in FIG. 2, horizontal tether receiving passageway 98 may define a third axis A3. In this example, third aperture 22 may define a horizontal tether receiving passageway 98 that extends in a direction that is substantially parallel to an extension direction of a longitudinal rod placed in the rod receiving cavity 3. For example, as seen best in FIG. 2, axes A3 and A1 are substantially parallel to one another. In various embodiments, the first aperture 20, second aperture 21, and third aperture 22 may be circular, rectangular, square, slotted, and any combination thereof.

Additionally, vertical tether receiving passageway 99 and horizontal tether receiving passageway 98 may intersect with one another and/or communicate with one another. As seen best in FIG. 2, axes A2 and A3 intersect one another. Additionally, with reference to FIG. 7, it may be seen that the vertical tether receiving passageway 99 may extend through a medial portion of horizontal tether receiving passageway 98. At least one advantage of this configuration may be that a single wedge 11 may be used to secure a tether extending through vertical tether receiving passageway 99 and/or horizontal tether receiving passageway 98 by pinning the tether against a common sidewall surface 96 (see FIG. 7), e.g., a bearing surface in a shared common space. In some embodiments, a surgeon may use a single tether to perform a first pass through one of passageways 99 or 98 and then perform a second pass through the other remaining passageway 99 or 98. In some surgical procedures, a first tether may extend through vertical tether receiving passageway 99 and a second tether may extend through horizontal tether receiving passageway 98.

Referring to the exploded parts view of FIG. 7, it may be seen that a cavity 19 is formed in the side portion 2 for receiving an immobilization assembly 97. Additionally, in FIG. 8A an exploded parts view of the immobilization assembly 97 is shown side by side with an assembled view of the immobilization assembly 97. Immobilization assembly 97 may comprise a set screw 10 that is disposed in a threaded aperture 5 such that the set screw may be rotated and travel up and down in a vertical direction. For example, as shown in FIG. 2, the set screw 10 may travel up and down in a vertical direction along axis A4. Additionally, in at least some embodiments as set screw 10 travels downward the tip of conical tip portion 14 may extend through relief aperture 31. This configuration has the advantage of minimizing a total height of receiver 100.

Set screw 10 may take any suitable size and shape such that as it moves up and down along axis A4, the set screw may directly contact a conically ramped surface 12 of wedge 11. In this way, as set screw 10 advances downward towards wedge 11 set screw 10 urges wedge 11 in a horizontal direction towards sidewall surface 96. For example, set screw 10 may be configured to move downward in a vertical direction along axis A4 thereby urging wedge 11 to slide in cavity 19 and in a horizontal direction along axis A5 (see FIG. 2). As seen best in FIG. 2, axes A4 and A5 are substantially perpendicular to one another. In this way, textured surface 13 (see FIGS. 8A-8B) may directly contact a tether extending through either the vertical passageway 99 and/or horizontal passageway 98 and immobilize the tether(s) by pinning it (them) against sidewall surface 96. Textured surface 13 may be a high friction surface that is a knurled surface, a textured surface comprising a plurality of protrusions, or a surface that is coated with a high friction coating. Similarly, sidewall surface 96 may be a high friction surface to further facilitate the immobilization of a tether.

In various embodiments, set screw 10 may include a conical tip portion 14 having a size and shape that generally corresponds to a size and shape of conically ramped surface 12 of wedge 11. For example, conical tip portion 14 may be a protrusion and conically ramped surface 12 may be a portion of a correspondingly shaped indentation, i.e., about half of a fully circumscribed conically shaped indentation as shown in FIG. 7. In various embodiments, set screw 10 and conical tip portion 14 may be integrally formed as a unitary component or they may be coupled together as separable components. In this example, set screw 10 is coupled to conical tip portion 14. For example, conical tip portion 14 may include a slotted aperture 17 extending through conical tip portion 14. In turn, plate 15 may be disposed in slotted aperture 17. A secondary smaller set screw 16 may extend through the interior drive aperture of set screw 10 to engage with aperture 18 of plate 15. For example, secondary set screw 16 may securely couple the conical tip portion 14 and set screw 10 via plate 15 as seen best in FIG. 8B.

In various embodiments, a first step of installation and/or operation may include initially securing the body 1 to the pedicle screw and thereafter securing the longitudinal rod within the U-shaped cavity. Once the body 1 and longitudinal rod are secured in position thereafter a surgeon may pass a tether through an aperture of the body 1 and tighten the tether. Additionally, it shall be understood that in some embodiments, the surgeon may pass the tether through an aperture of the body 1 before securing the body 1 to the pedicle screw and/or rod. In summary, embodiments in accordance with the principles herein provide a surgeon with the capability of performing different installation sequences, e.g., the tether may be passed either before, after, or even concurrently with securing body 1 to the pedicle screw.

Figure 9:
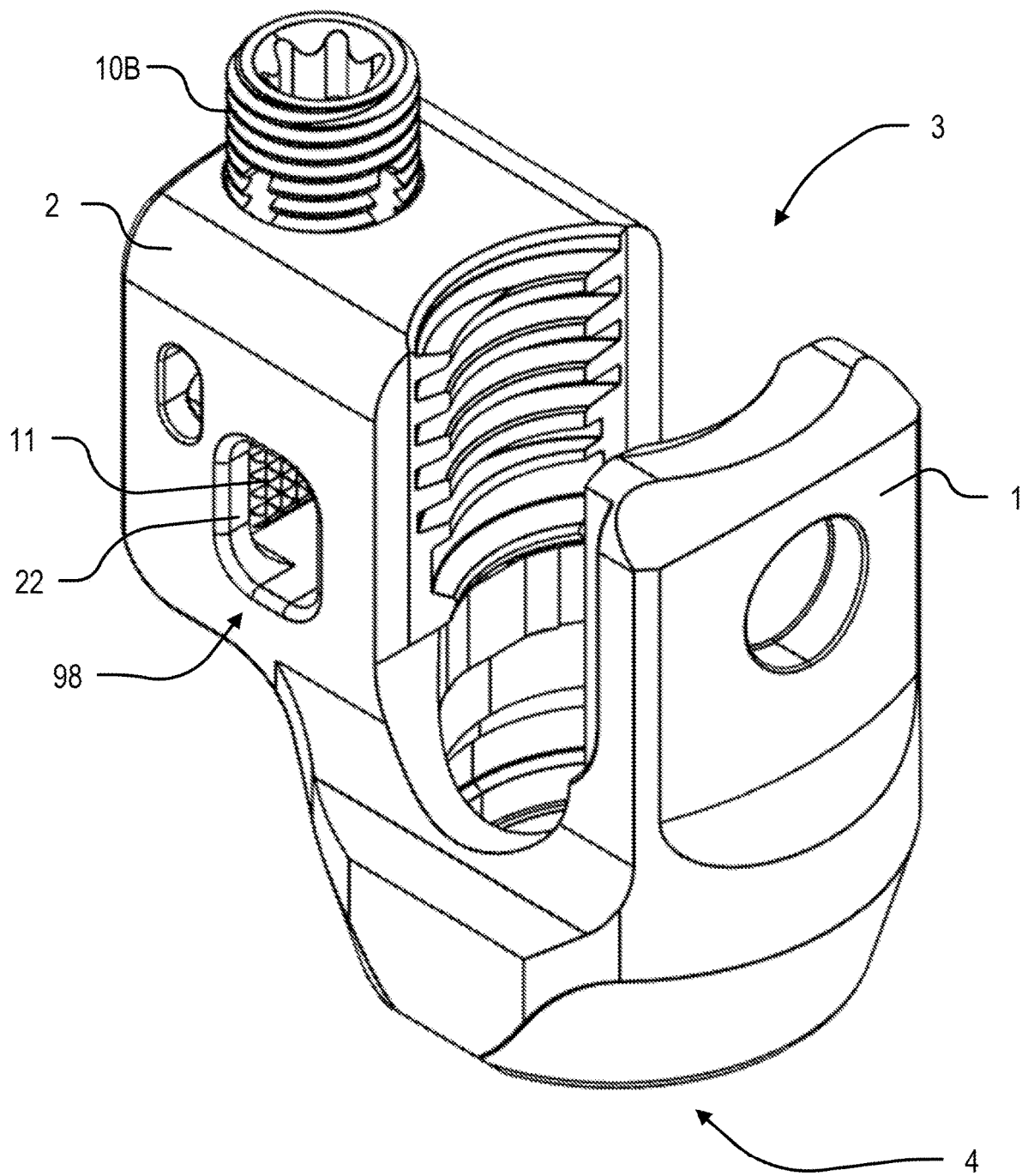
FIG. 9 is a perspective view of a second multiaxial receiver embodiment.
Figure 10:
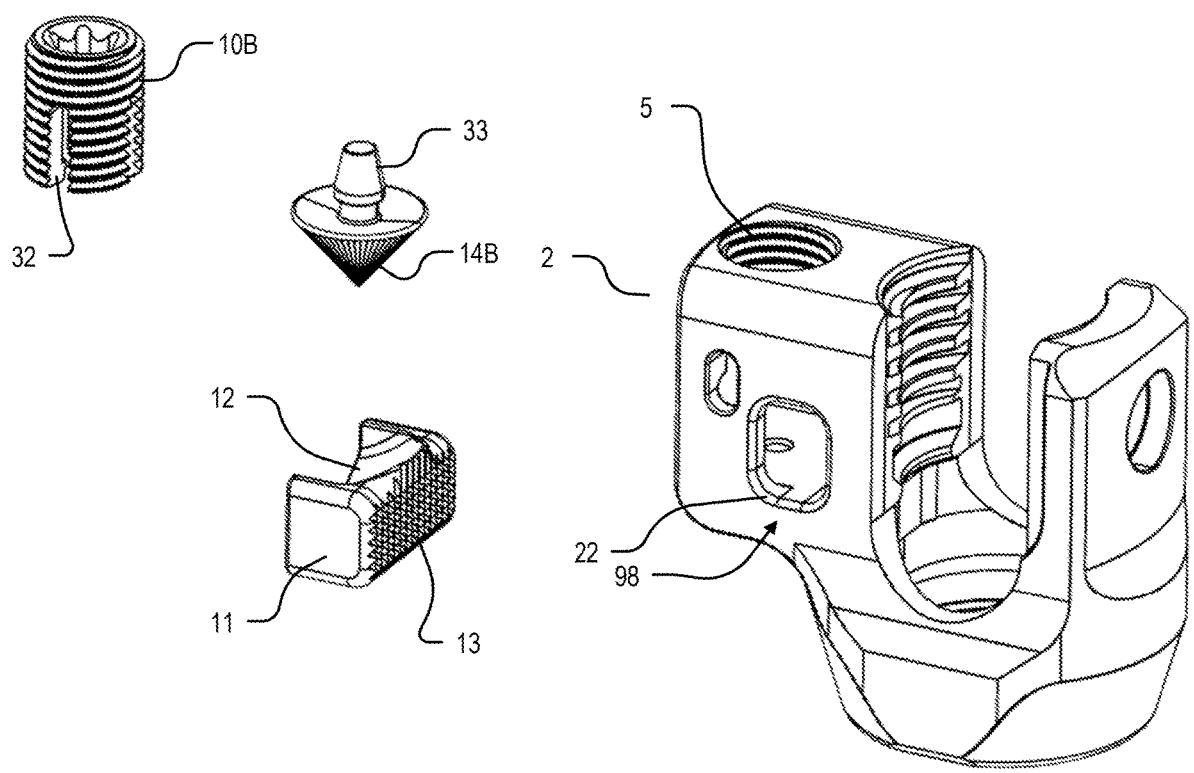
FIG. 10 is an exploded parts view of the second multiaxial receiver embodiment of FIG. 9.

FIG. 9 is a perspective view of a second multiaxial receiver 101 and FIG. 10 is an exploded parts view of the second receiver 101. Multiaxial receiver 101 may include the same, similar, and/or substantially the same components and functionality as explained above with respect to multiaxial receiver 100. Accordingly, duplicative description will be omitted. In this embodiment multiaxial receiver 101 may differ in that it does not include the vertical tether receiving passageway 99, top aperture 20, and bottom aperture 21. An advantage of this embodiment may be a reduction in size of the second portion 2 and an alternately configured immobilization assembly 97.

Figure 11A:
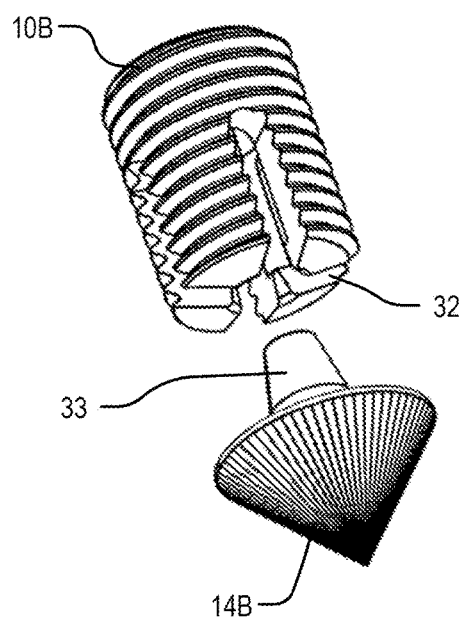
FIG. 11A is an exploded parts view of a second immobilization assembly.
Figure 11B:
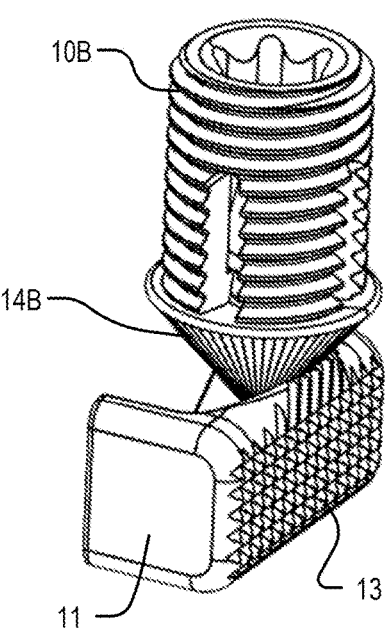
FIG. 11B is an assembled parts view of the immobilization assembly of FIG. 11A.

Referring generally to FIGS. 10, 11A, and 11B a second immobilization assembly 97B is disclosed. In this embodiment, set screw 10B may include at least one cutout 32 at a lower end of the set screw 10B. In the example embodiment, four cutouts 32 are evenly spaced around the circumference of the set screw 10B. These cutouts may allow set screw 10B to elastically deform such that conical tip 14B may be coupled to set screw 10B by a snap fit or press fit configuration. For example, a flattened point conical protrusion 33 may snap fit into a bore on the bottom of set screw 10B. During an insertion of protrusion 33 into set screw 10B the cutouts 32 may temporarily flare out and then come back together when protrusion 33 is inserted sufficiently far into set screw 10B.

Figure 12A:
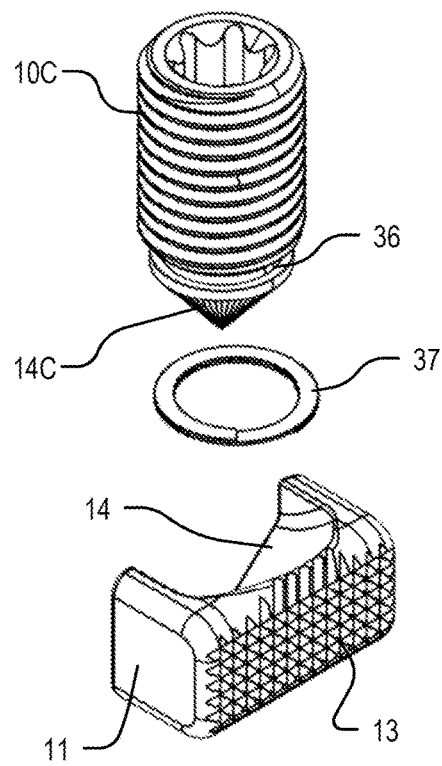
FIG. 12A is an exploded parts view of a third immobilization assembly.
Figure 12B:
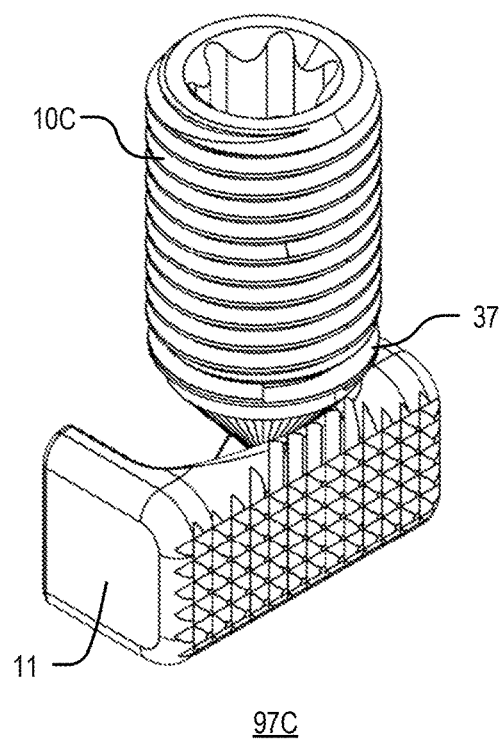
FIG. 12B is an assembled parts view of the immobilization assembly of FIG. 12A.

Referring generally to FIGS. 12A and 12B a third immobilization assembly 97C is disclosed. Immobilization assembly 97C may be used in any of the various multiaxial receivers disclosed herein. In this embodiment, set screw 10C may include a lower channel 36 for mating with a C-ring 37. In this embodiment, set screw 10C may be integrally formed with conical tip 14C. In various embodiments, set screw 10C may be formed by a subtractive manufacturing process in which conical tip portion 14C is formed by removing material from an elongated set screw 10C. In this way, a cross sectional diameter of the threaded portion of set screw 10C is greater than a cross sectional diameter of the conical tip portion 14C. This embodiment may have advantages in terms of manufacturing and durability, but it may result in a situation in which set screw 10C can inadvertently back out. To address this backing out issue, C-ring 37 may be mated to lower channel 36 to prevent set screw 10C from backing out of threaded aperture 5 (see FIG. 10). For example, a cross sectional diameter of c ring 37 is greater than a maximum cross-sectional diameter of set screw 10C. In other embodiments, a first end of conical tip 14C may be partially inserted into set screw 10C and then the c ring 37 may mate the conical tip 14C together with the set screw 10C.

Figure 13A:
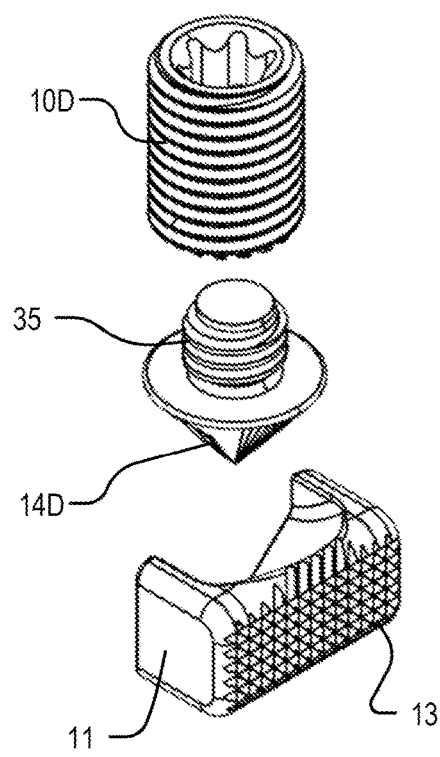
FIG. 13A is an exploded parts view of a fourth immobilization assembly.
Figure 13B:
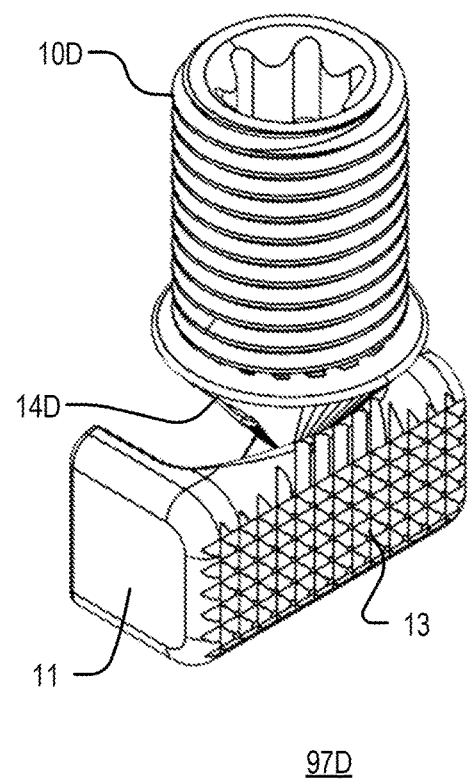
FIG. 13B is an assembled parts view of the immobilization assembly of FIG. 13A.

FIG. 13A is an exploded parts view of a fourth immobilization assembly 97D and FIG. 13B is an assembled parts view of the immobilization assembly 97D. Immobilization assembly 97D may be used in any of the various multiaxial receivers disclosed herein. In various embodiments, set screw 10D may include a threaded aperture in the lower end thereof for receiving a threaded protrusion 35 of conical tip 14D. For example, the threaded protrusion 35 may have a thread pattern that corresponds in size and shape to an internal thread pattern of set screw 10D.

Figure 14:
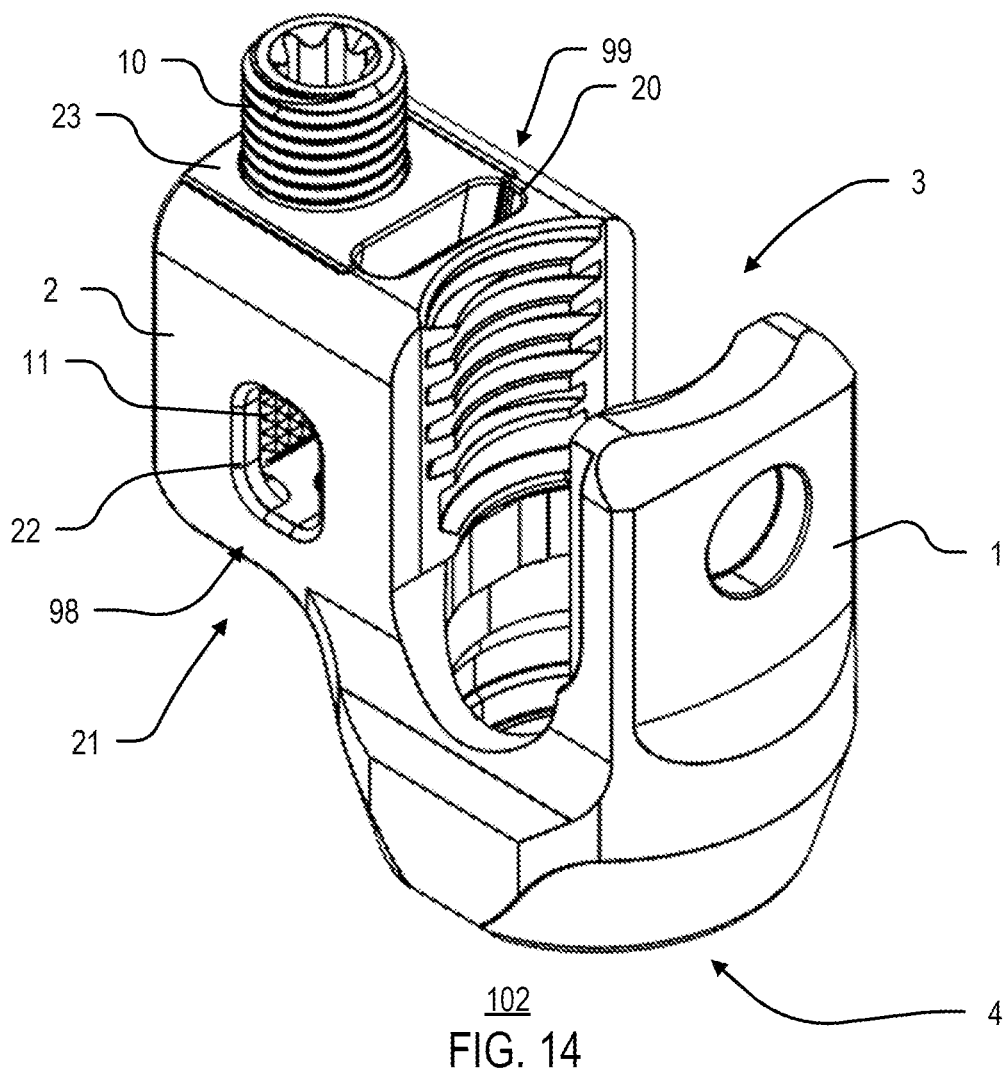
FIG. 14 is a perspective view of a third multiaxial receiver embodiment.
Figure 15:
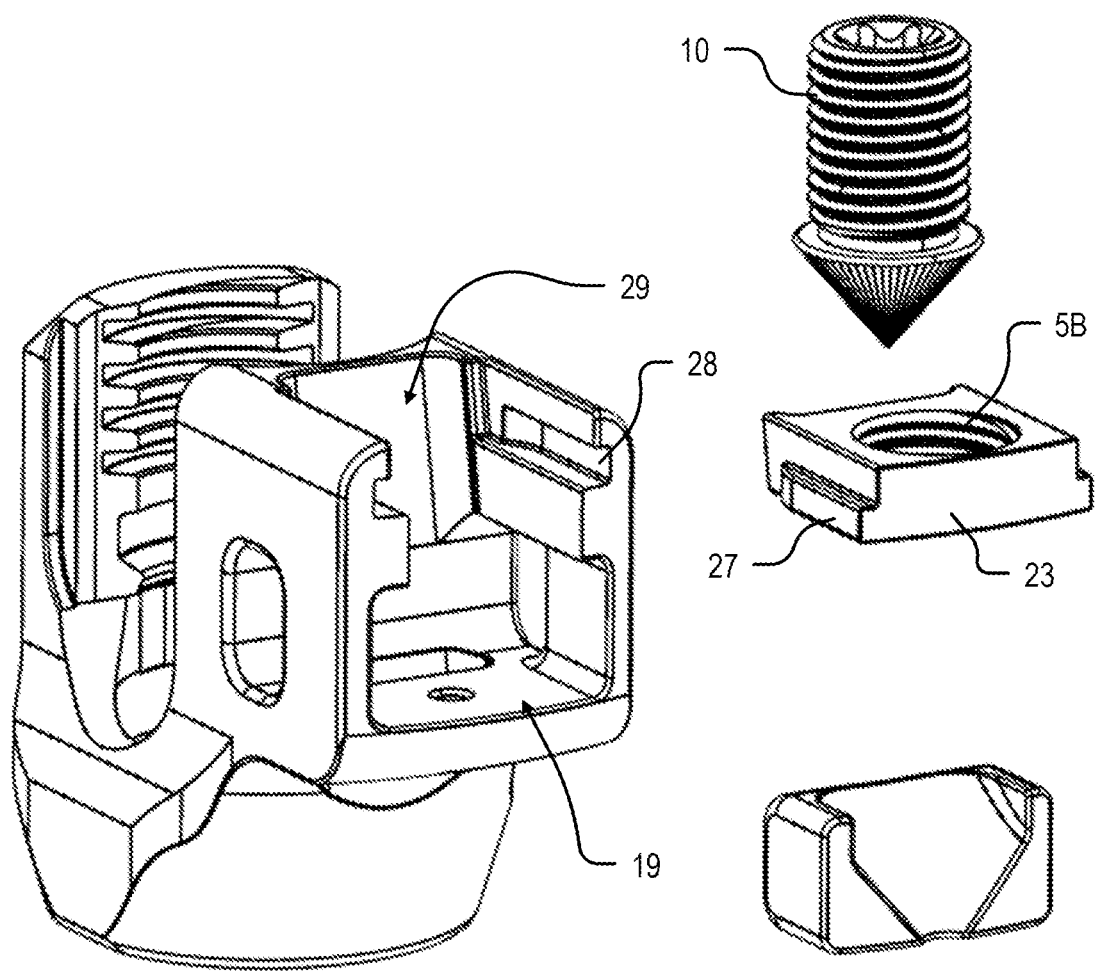
FIG. 15 is an exploded parts view of the third multiaxial receiver embodiment of FIG. 14.

FIG. 14 is a perspective view of a third multiaxial receiver embodiment 102 and FIG. 15 is an exploded parts view of the third multiaxial receiver embodiment 102. Multiaxial receiver 102 may include the same, similar, and/or substantially the same components and functionality as explained above with respect to multiaxial receivers 100 and 101. Accordingly, duplicative description will be omitted. In this embodiment multiaxial receiver 102 may differ in that it includes a top plate 23 which may secure to side portion 2. As seen best in FIG. 15, top plate 23 may include rails 27 that allow top plate 23 to be mated with in top cavity 29 via the slots 28. For example, slots 28 may have a corresponding size and shape to the size and shape of rails 27 and an overall size and shape of plate 23 may correspond to an overall size and shape of top cavity 29. Additionally, top plate 23 may include a threaded aperture 5B for supporting set screw 10 therein. At least one advantage to this configuration may be adjustability and an increased cavity space on account of top cavity 29 and lower cavity 19 together forming a relatively larger space. In various embodiments, once top plate 23 is mated to side portion 2 and set screw 10 is disposed within aperture 5B, the top plate 23 may be welded and/or otherwise immovably fixed to side portion 2.

Referring generally to FIGS. 16-21B a fourth multiaxial receiver embodiment 200 is disclosed. This embodiment may share many of the same and/or similar features and functionality as explained above with respect to multiaxial receiver embodiments 100, 101, and 102. Accordingly, duplicative description will be omitted. Fourth multiaxial receiver 200 may differ in that it includes a breakoff set screw 40 having a fracture surface 41 (see FIG. 17) and alternately configured horizontal and vertical tether receiving passageways 98, 99.

Figure 16:
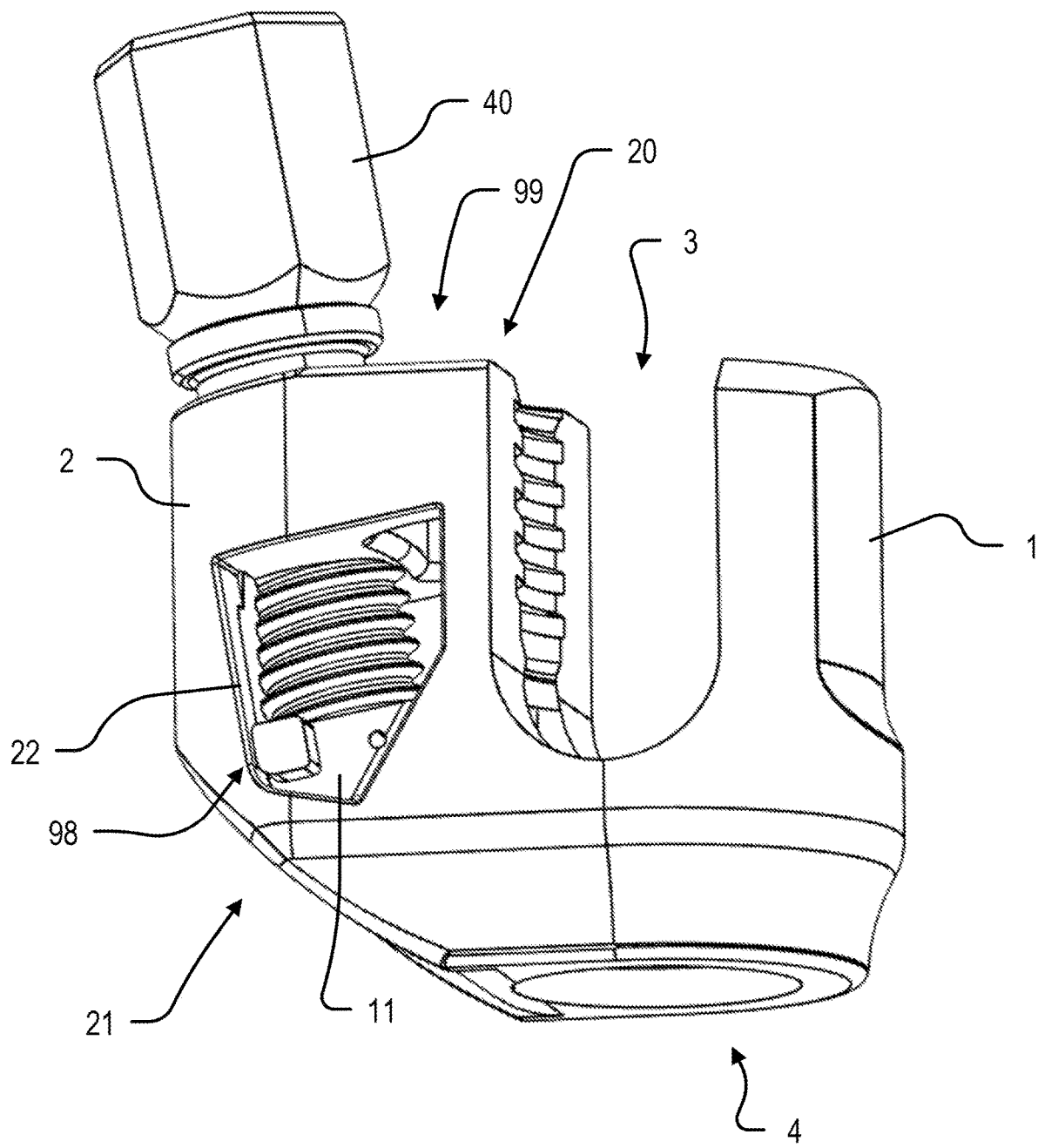
FIG. 16 is a perspective view of a fourth multiaxial receiver embodiment.
Figure 17:
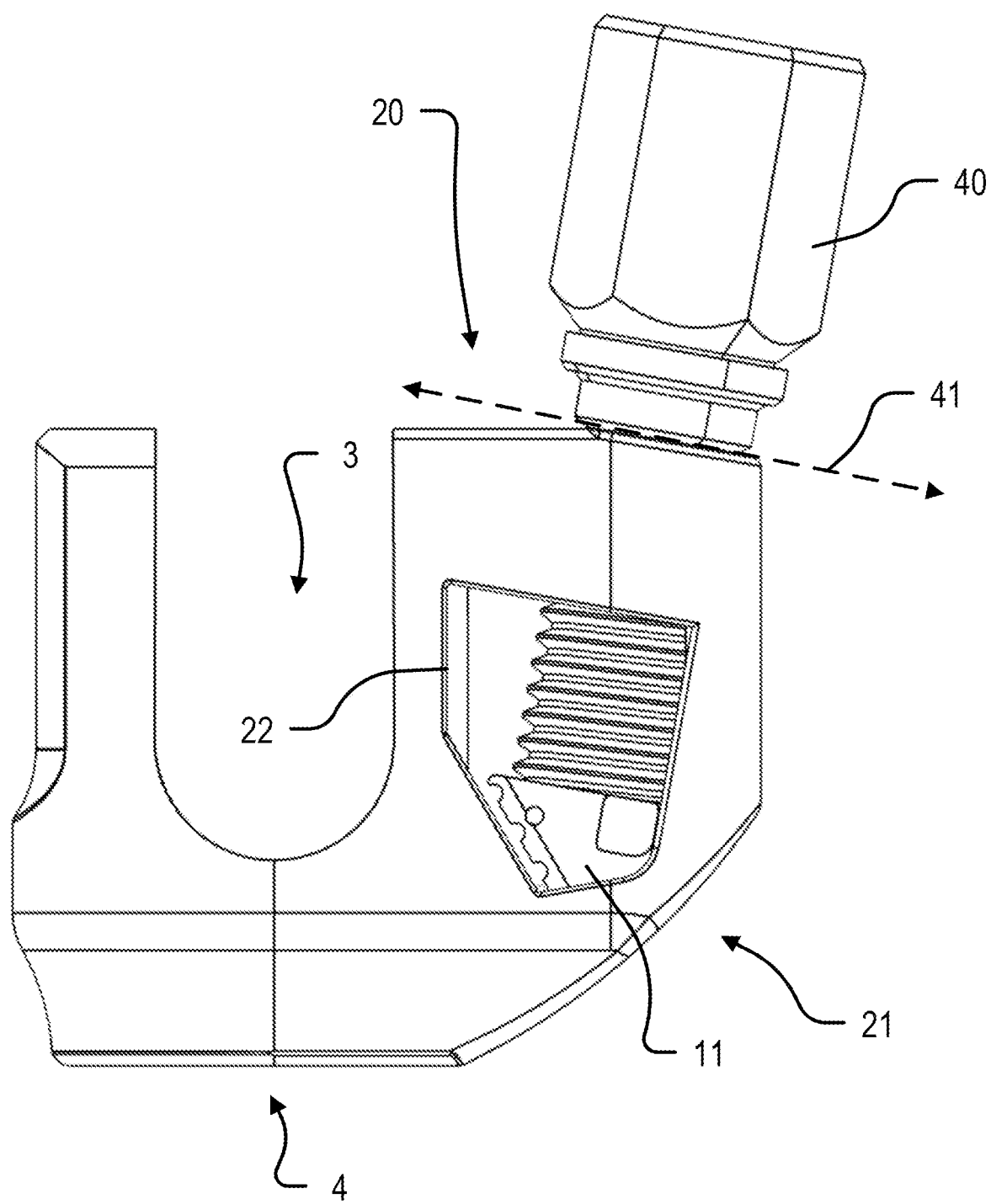
FIG. 17 is a side view of the fourth multiaxial receiver embodiment of FIG. 16.
Figure 18:
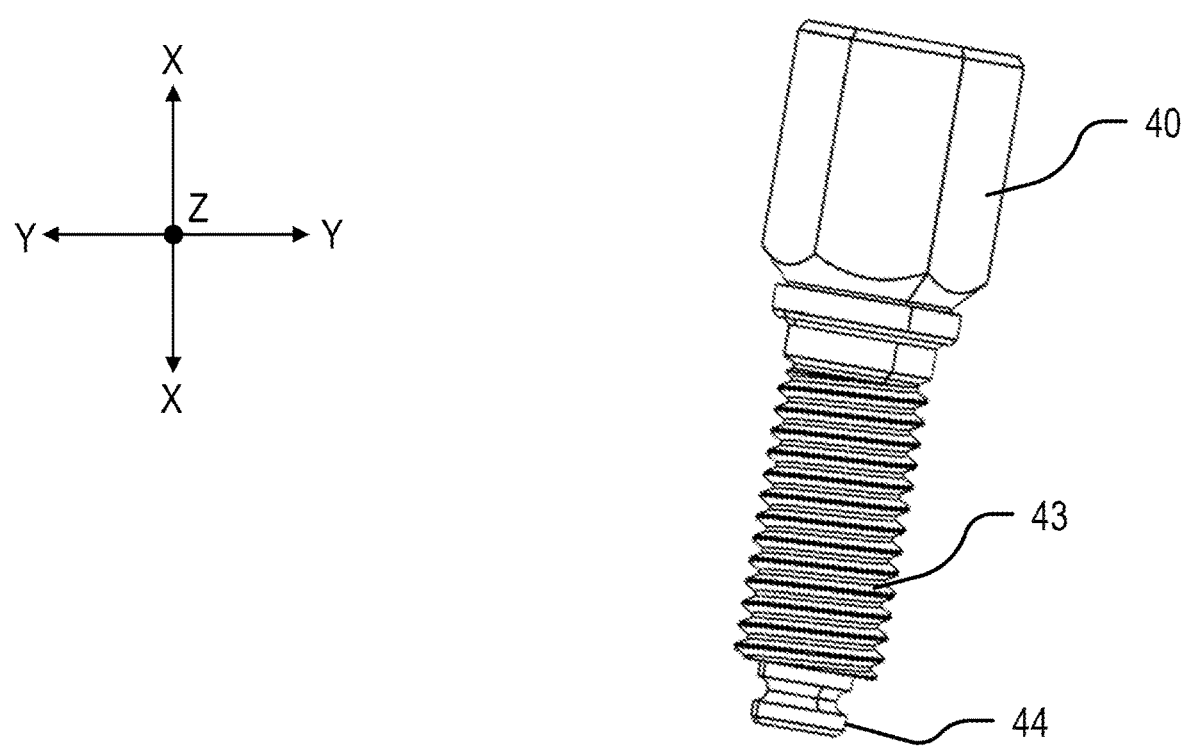
FIG. 18 is an exploded parts view of the fourth multiaxial receiver embodiment of FIG. 16.
Figure 18:
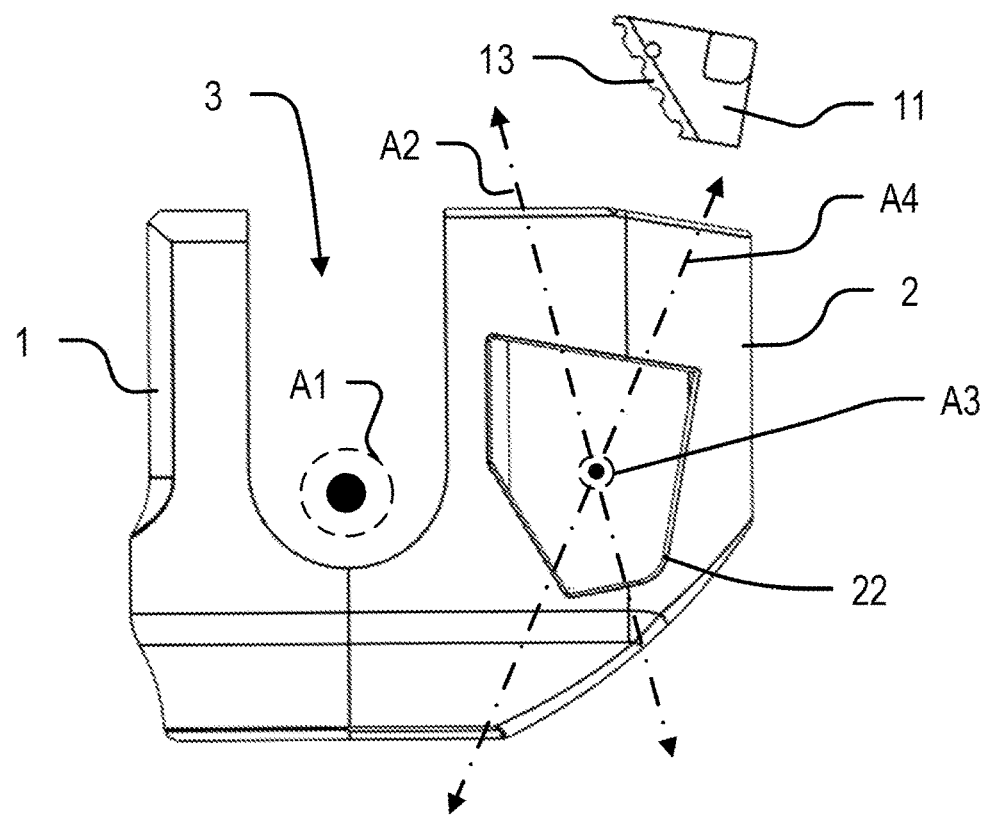
Figure 19:
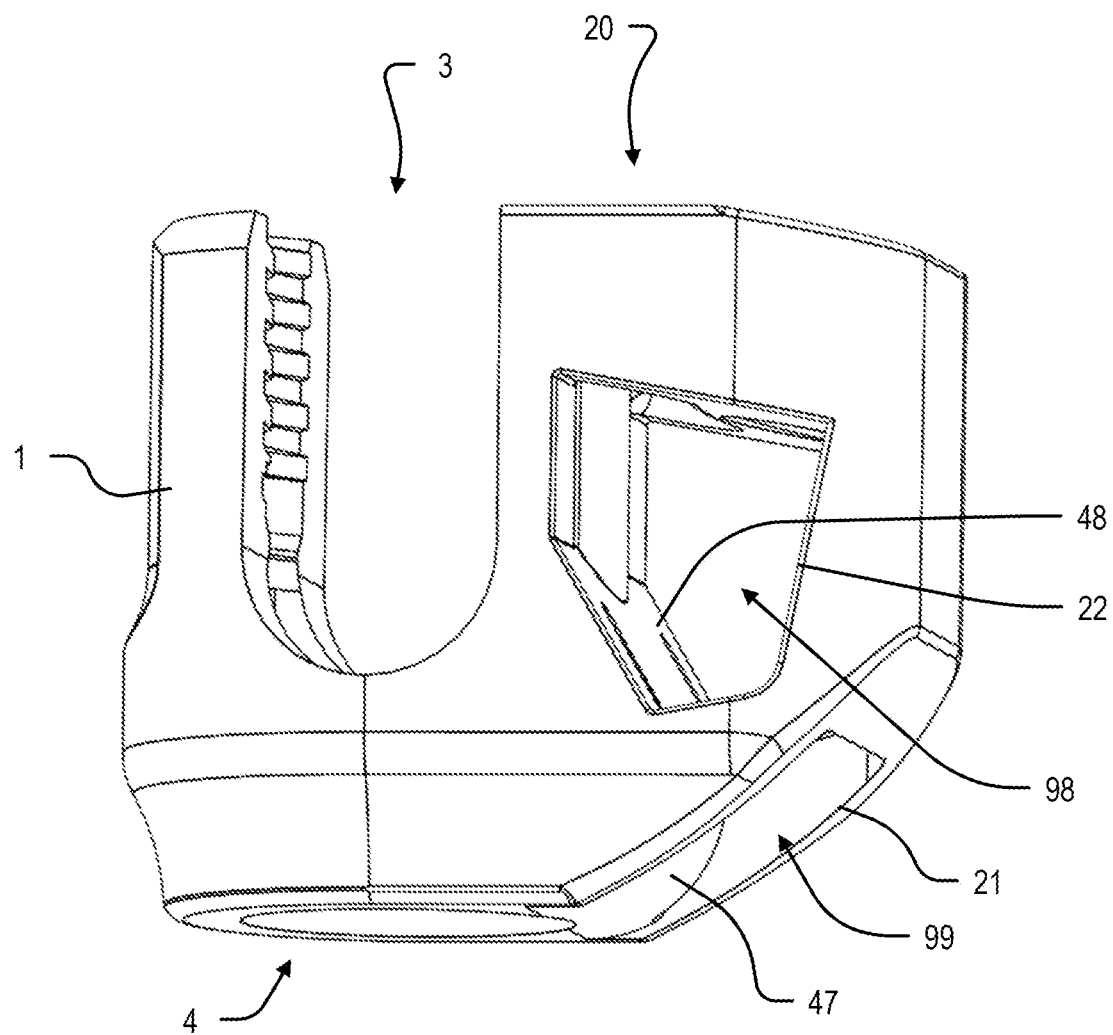
FIG. 19 is a partial parts side view of the fourth multiaxial receiver embodiment of FIG. 16.
Figure 20A:
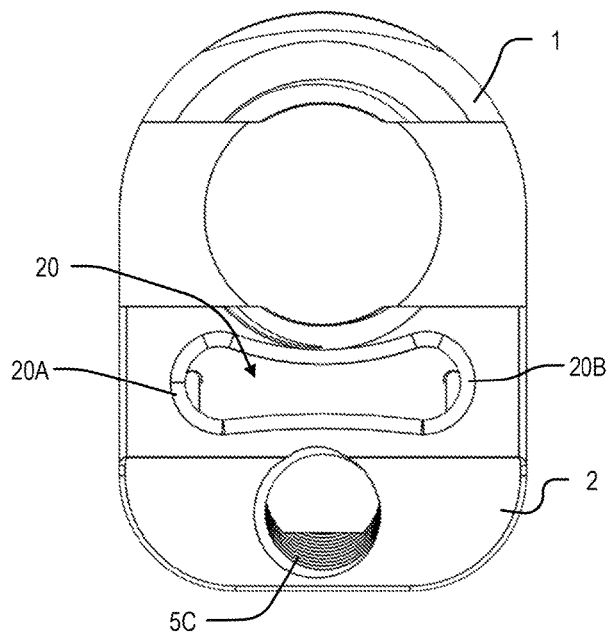
FIG. 20A is a partial parts top view of the fourth multiaxial receiver embodiment of FIG. 16.
Figure 20B:
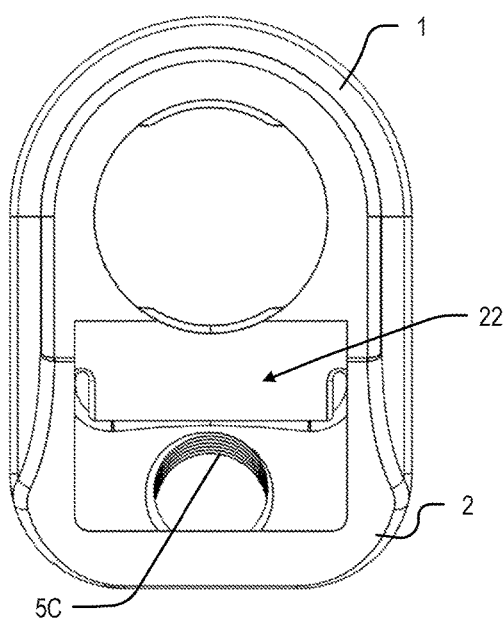
FIG. 20B is a partial parts bottom view of the fourth multiaxial receiver embodiment of FIG. 16.
Figure 21A:
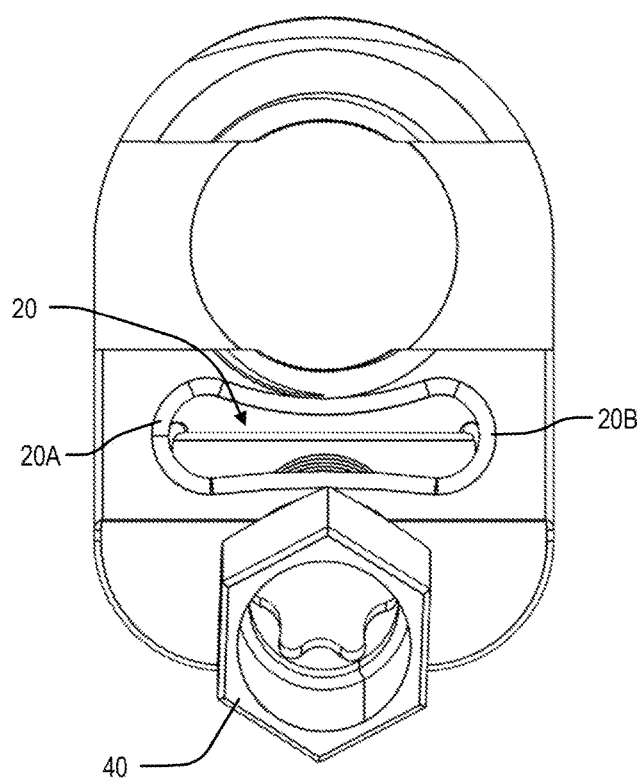
FIG. 21A is an assembled top view of the fourth multiaxial receiver embodiment of FIG. 16.
Figure 21B:
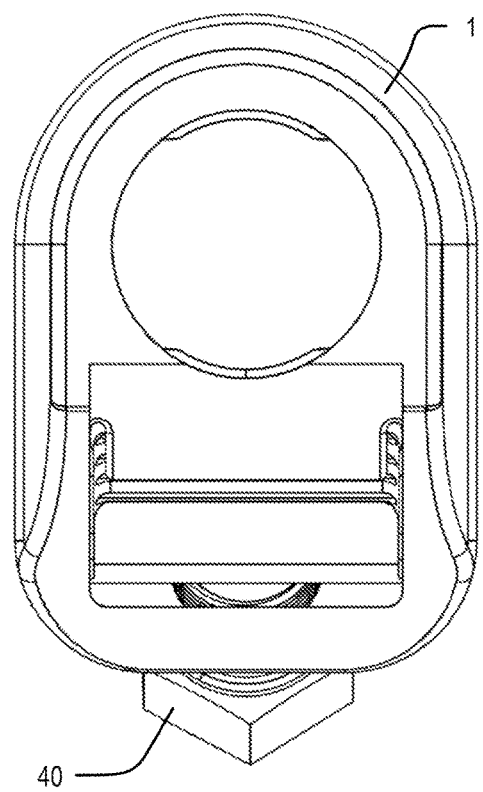
FIG. 21B is an assembled bottom view of the fourth multiaxial receiver embodiment of FIG. 16.

FIG. 16 is a perspective view of the fourth multiaxial receiver 200, FIG. 17 is a side view, FIG. 18 is an exploded parts view, FIG. 19 is a partial parts side view, FIG. 20A is a partial parts top view, FIG. 20B is a partial parts bottom view, FIG. 21A is an assembled top view, and FIG. 21B is an assembled bottom view. In the example embodiment, multiaxial receiver 200 may include a vertical tether receiving passageway 99 defined by a top aperture 20 and a bottom aperture 22. Additionally, multiaxial receiver 200 may include a horizontal tether receiving passageway 98 defined by aperture 22. As seen best in FIG. 18, set screw 40 may include a breakoff head, a threaded shaft 43, and a coupling protrusion 44. In disclosed embodiments, coupling protrusion 44 may secure to wedge 11 by any means, e.g., snap fit, pressure fit, friction fit, adhesion, weld, etc.

With reference to FIGS. 16 and 18, vertical tether receiving passageway 99 and horizontal tether receiving passageway 98 may intersect with one another and/or communicate with one another. As seen best in FIG. 18, axes A1 may be defined by a longitudinal rod (not illustrated), axes A2 may be defined by the vertical tether receiving passageway 99 and angle of repose of the threaded aperture 5C (see FIGS. 20A-21B), axis A3 may be defined by the horizontal tether receiving passageway 98 and axis A4 may be defined by a path of travel of breakoff set screw 40. As may also be seen in FIG. 18, axes A2 and A3 may communicate with one another and/or intersect one another. For example, it may be seen that the vertical tether receiving passageway 99 may extend through a medial portion of horizontal tether receiving passageway 98. At least one advantage of this configuration may be that a single wedge 11 may be used to secure a tether extending through vertical tether receiving passageway 99 and/or horizontal tether receiving passageway 98 by pinning the tether against a common sidewall surface 48 (see FIG. 19).

As seen best in FIG. 19, common sidewall surface 48 may be angled with respect to the vertical direction and surface 13 of wedge 11 may be angled at a similar corresponding extent. Additionally, bottom aperture 21 may expose ramped surface 47 which may facilitate passing a tether therethrough and orienting a tether appropriately for immobilization against the angled common sidewall surface 48. In some embodiments, a surgeon may use a single tether to perform a first pass through one of passageways 99 or 98 and then perform a second pass through the other remaining passageway 99 or 98. In some surgical procedures, a first tether may extend through vertical tether receiving passageway 99 and a second tether may extend through horizontal tether receiving passageway 98.

Referring to FIGS. 20A and 20B, it is shown that top aperture 20 may be a slotted aperture extending between a first bulbous end 20A and a second bulbous end 20B. These bulbous ends 20A, 20B may each form a respective pocket in which a tether may apply force against. For example, these bulbous ends 20A, 20B may facilitate a surgical operation in which the tether may more easily pass and/or be substantially oriented towards one of the two bulbous ends rather than centered within aperture 20. FIGS. 21A and 21B illustrate the same configurations of FIGS. 20A and 20B but with the set screw 40 installed.

Figure 22:
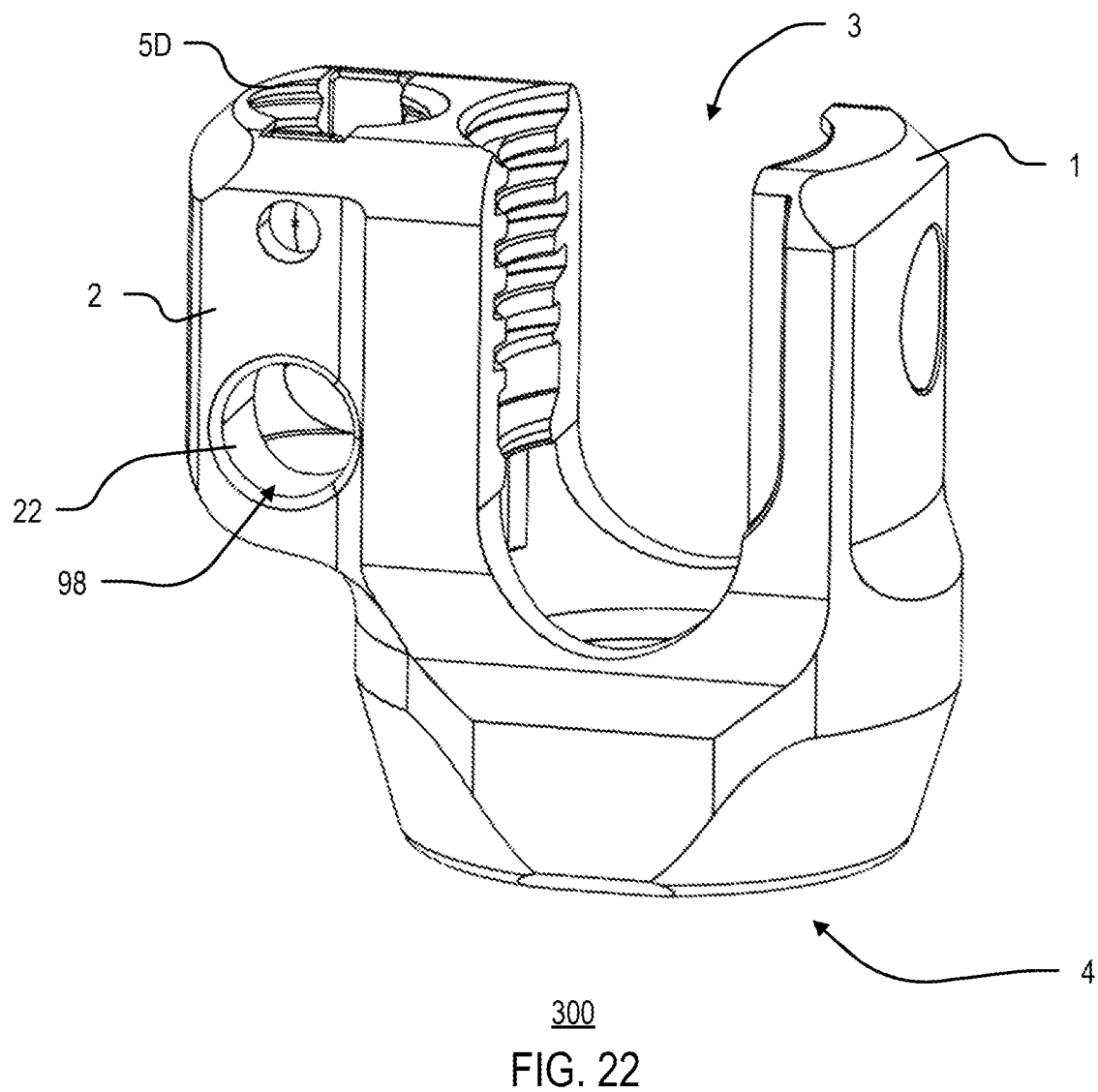
FIG. 22 is a perspective view of a fifth multiaxial receiver embodiment.
Figure 23:
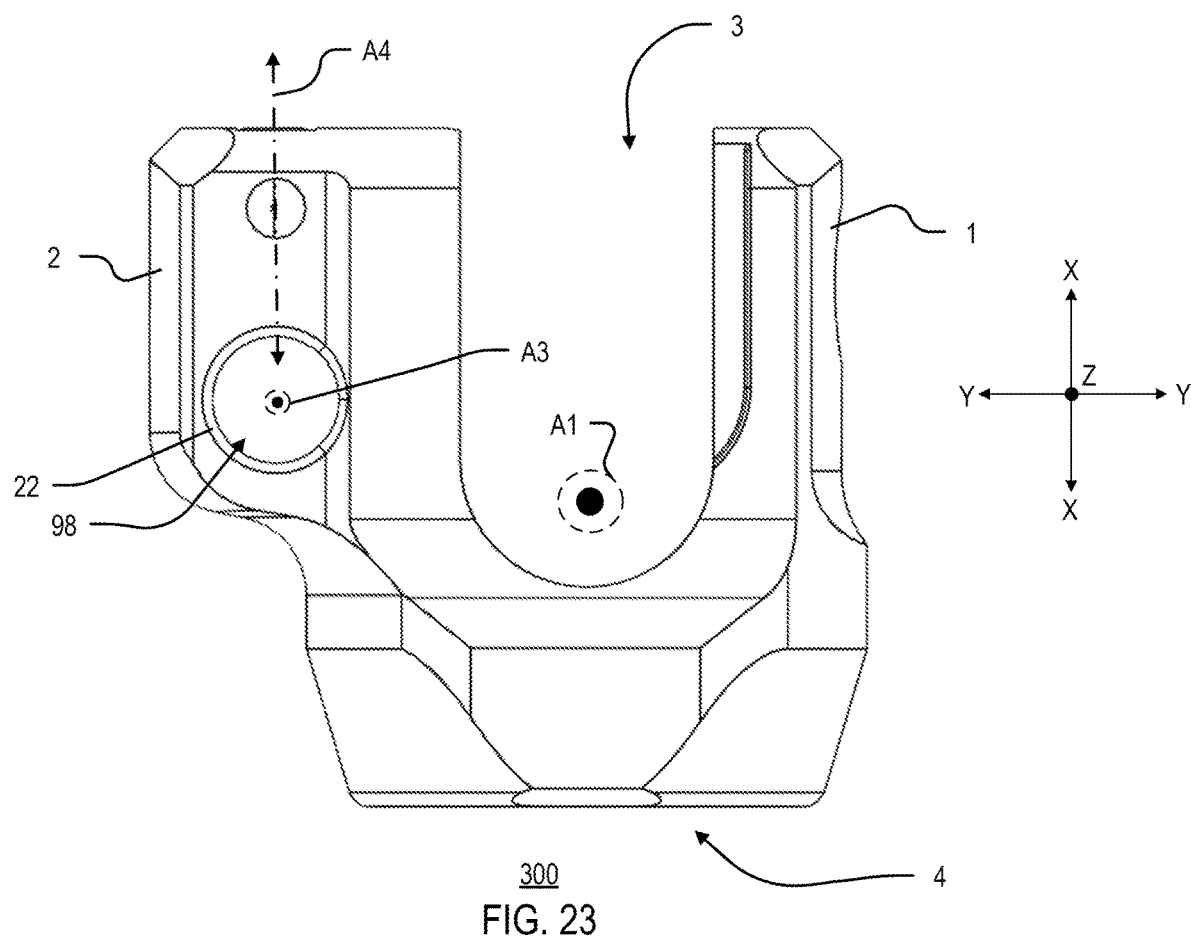
FIG. 23 is a side view of the fifth multiaxial receiver embodiment of FIG. 22.
Figure 24:
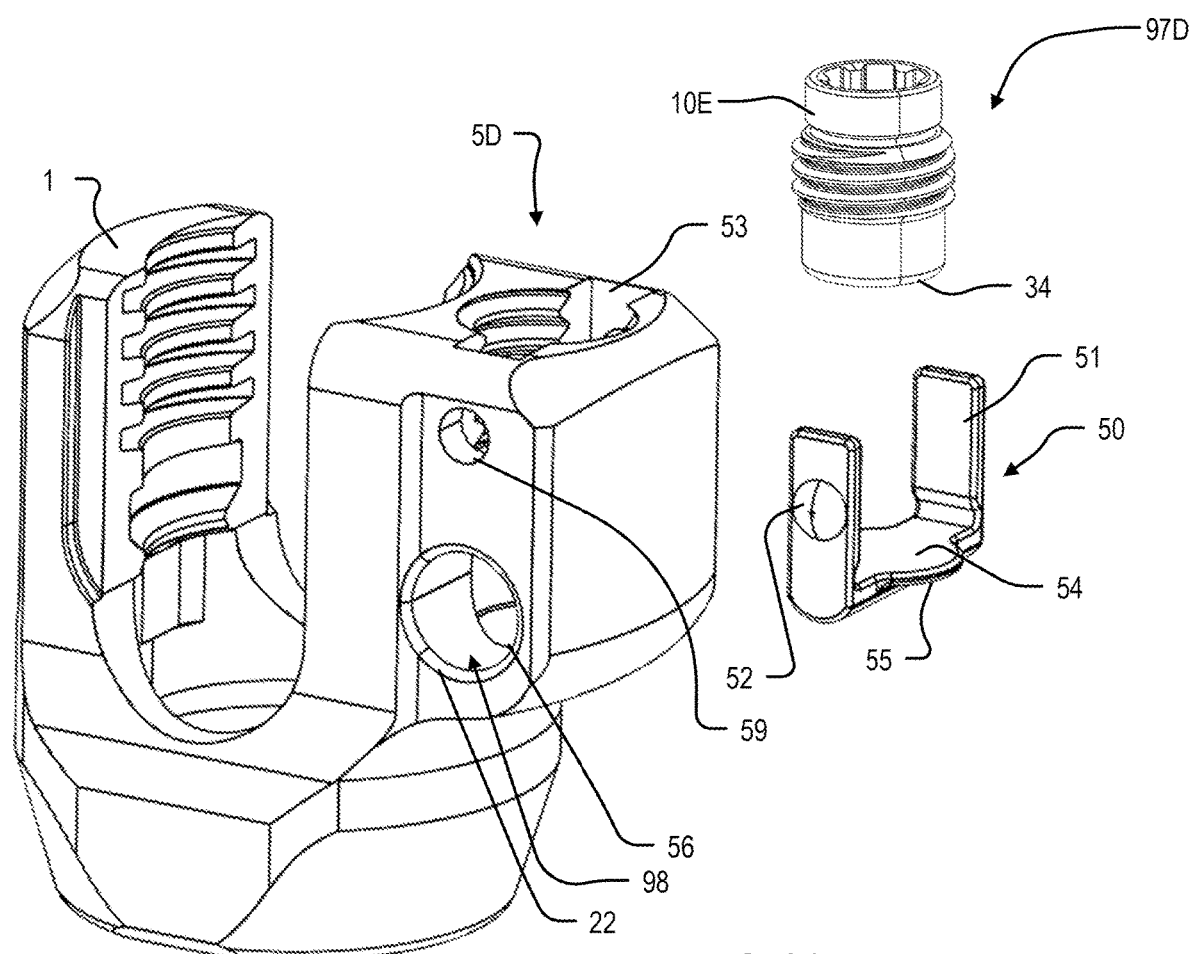
FIG. 24 is an exploded parts side view of the fifth multiaxial receiver embodiment of FIG. 22.
Figure 25:
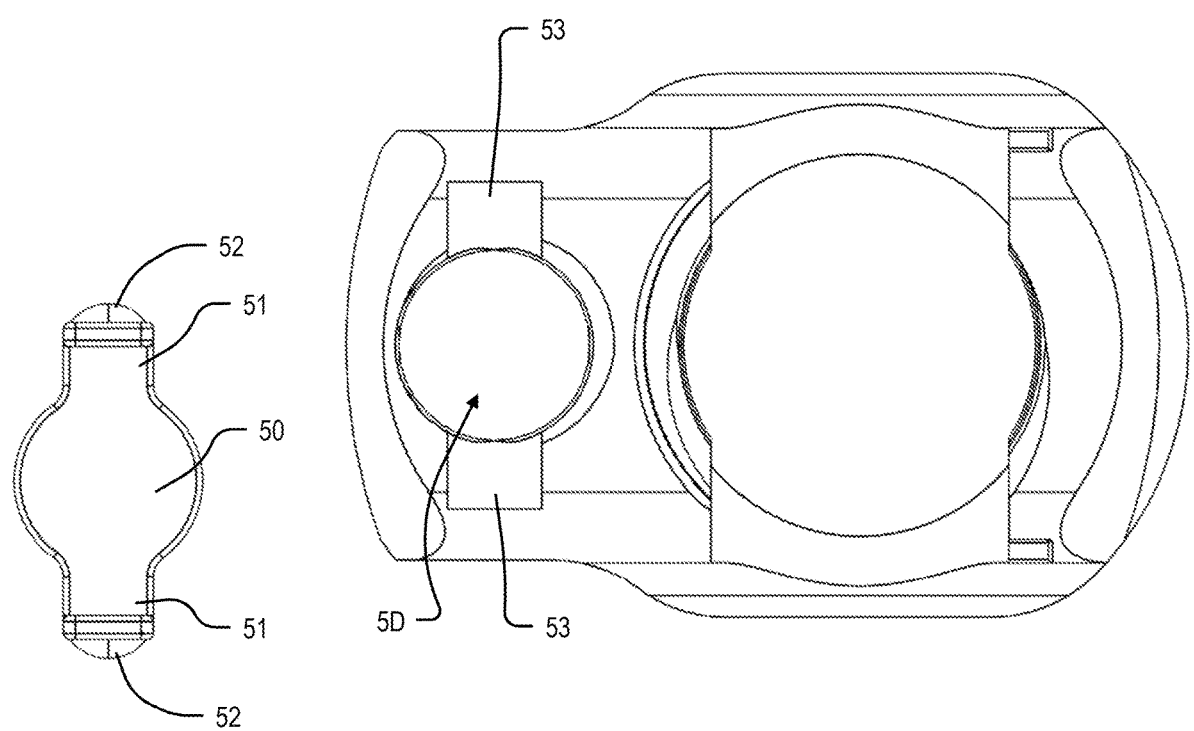
FIG. 25 is a top view of the fifth multiaxial receiver embodiment of FIG. 22.

Referring generally to FIGS. 22-25, a fifth multiaxial receiver embodiment 300 is disclosed. This embodiment may share many of the same and/or similar features and functionality as explained above with respect to multiaxial receiver embodiments 100, 101, 102, and 200. Accordingly, duplicative description will be omitted. This embodiment may differ in that it includes a single aperture 22 extending through side portion 2 in a horizontal direction and a differently configured immobilization assembly 97D. FIG. 22 is a perspective view of the fifth multiaxial receiver 300, FIG. 23 is a side view, FIG. 24 is an exploded parts side view, and FIG. 25 is a top view.

With reference to the exploded parts view of FIG. 24, multiaxial receiver 300 may include an immobilization assembly 97D. Immobilization assembly 97D may include a set screw 10E having a substantially flat planar bottom surface 34 and a winged wedge 50 also having a substantially flat planar screw contact surface 54 and substantially flat planar bottom surface 55. In this embodiment, wedge 50 may include a pair of oppositely disposed tabs 51 extending in a vertical direction from contact surface 54. Additionally, each tab may include a corresponding hemispherical shaped protrusion 52. In operation, wedge 50 may be disposed inside of threaded aperture 5D such that tabs 51 are disposed inside of vertical rails 53 and hemispherical shaped protrusions 52 are seated within positioning aperture 59 (see also top-down view of FIG. 25). In this way, vertical rails 53 may constrain wedge 50 from rotating and allow for movement of wedge up and down in a vertical direction. Additionally, a location of positioning aperture 59 may establish an initial open position of wedge 50 in the vertical direction such that a tether may freely pass through aperture 22 and horizontal tether receiving passageway 98. In operation, set screw 10E may be rotated such that it travels downward in a vertical direction towards horizontal tether receiving passageway 98. As set screw 10E travels downward, set screw 10E bottom surface 34 directly contacts a corresponding surface 54 of wedge 50 thereby urging wedge 50 downward as well. When a sufficient downward force is applied to wedge 50, tabs 51 may deform inwards towards one another thereby unseating hemispherical protrusion 52 from positioning aperture 59. In doing so, wedge 50 may freely travel downward such that bottom planar surface 55 may pin a tether against a corresponding planar bottom surface 56 of horizontal tether receiving passageway 98.

Referring to FIG. 23, axis A1 may be defined by a longitudinal rod (not illustrated), axis A3 may be defined by the horizontal tether receiving passageway 98 and axis A4 may be defined by a path of travel of set screw 10E and wedge 50. In this embodiment, a path of travel of set screw 10E may be substantially perpendicular to an orientation of the longitudinal rod and an extension direction of horizontal tether receiving passageway 98 may be substantially parallel to the orientation of the longitudinal rod.

Various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A multiaxial receiver, comprising:
   a body having a U-shaped cavity configured to receive a longitudinal rod therein and a lower cavity configured to couple to a pedicle screw, the body extending in a vertical direction along a longitudinal axis and extending horizontally along a widthwise axis;
   a side portion including a first aperture on an upper surface thereof and a second aperture on a bottom surface thereof, the first and second apertures together defining a first passageway configured to permit a tether to pass therethrough in the vertical direction;
   a threaded aperture extending through the upper surface and into the first passageway; and
   an immobilization assembly including a set screw and a wedge, the set screw being disposed within the threaded aperture, wherein the set screw includes a conical tip configured to directly contact a conically shaped surface of the wedge;
   wherein the immobilization assembly is configured to be rotated from an open position in which the tether is permitted to pass through the first passageway to a closed position in which the tether is immobilized within the first passageway, and wherein in the closed position, the wedge is configured to pin the tether against a bearing surface of the first passageway.

2. The multiaxial receiver of claim 1, wherein the lower cavity is configured to mate to a head of the pedicle screw that permits the multiaxial receiver to be angled with respect to an extension direction of the pedicle screw.

3. The multiaxial receiver of claim 1, wherein the conical tip is configured to extend through a receiving aperture in the bottom surface of the side portion.

4. The multiaxial receiver of claim 1, wherein the conical tip is integrally formed with the set screw.

5. The multiaxial receiver of claim 1, wherein the conical tip is configured to couple to the set screw.

6. The multiaxial receiver of claim 5, wherein:
the set screw comprises a lower cavity and a plurality of cutouts surrounding the lower cavity, and
the conical tip comprises a first end having a protrusion for mating to the lower cavity of the set screw via a snap fit and a second end having a pointed end.

7. The multiaxial receiver of claim 5, wherein:
the immobilization assembly further comprises a secondary set screw and a positioning plate,
the secondary set screw being threaded to an inside portion of the set screw and coupled to the positioning plate, and
the positioning plate extending through a slotted aperture of the conical tip such the conical tip is coupled to the set screw and the secondary set screw.

8. The multiaxial receiver of claim 1, further comprising a C-clamp that surrounds a portion of the conical tip.

9. The multiaxial receiver of claim 1, wherein the set screw comprises a lower cavity including a thread pattern thereon and the conical tip comprises an upper protrusion having a thread pattern thereon, the upper protrusion corresponding in size and shape to a size and shape of the lower cavity of the set screw.

10. The multiaxial receiver of claim 1, wherein the wedge comprises a knurled surface and the bearing surface is substantially flat.

11. The multiaxial receiver of claim 1, wherein the set screw is a breakoff set screw.

12. A multiaxial receiver, comprising:
a body having a U-shaped cavity configured to receive a longitudinal rod therein and a lower cavity configured to couple to a pedicle screw, the body extending in a vertical direction along a longitudinal axis and extending horizontally along a widthwise axis;
a side portion including a first aperture extending through a side surface thereof and defining a first passageway configured to permit a tether to pass therethrough in the horizontal direction;
a threaded aperture extending through the upper surface and into the first passageway; and
an immobilization assembly including a set screw and a wedge, the set screw being disposed within the threaded aperture, wherein the set screw includes a conical tip configured to directly contact a conically shaped surface of the wedge;
wherein the immobilization assembly is configured to be rotated from an open position in which the tether is permitted to pass through the first passageway to a closed position in which the tether is immobilized within the first passageway, and
wherein in the closed position, the wedge is configured to pin the tether against a bearing surface of the first passageway.

13. The multiaxial receiver of claim 12, wherein the lower cavity is configured to mate to a head of the pedicle screw that permits the multiaxial receiver to be angled with respect to an extension direction of the pedicle screw.

14. The multiaxial receiver of claim 12, wherein the set screw comprises a substantially planar lower surface configured to directly contact a planar surface of the wedge.

15. The multiaxial receiver of claim 14, wherein:
the threaded aperture includes a plurality of slots extending in the vertical direction,
the wedge includes a plurality of tabs, each tab having a hemispherical protrusion,
the side portion includes a plurality of positioning apertures, and
each tab being disposed within one corresponding slot such that rotation of the wedge is prevented, and each hemispherical protrusion being disposed inside one corresponding positioning aperture.

16. The multiaxial receiver of claim 15, wherein the conical tip is configured to couple to the set screw.

17. A multiaxial receiver, comprising:
a body having a U-shaped cavity configured to receive a longitudinal rod therein and a lower cavity configured to couple to a head of a pedicle screw that permits multiaxial orientation of the body with respect to an extension direction of the pedicle screw, the body extending in a vertical direction along a longitudinal axis and extending horizontally along a widthwise axis;
a side portion including a first passageway configured to permit a tether to pass therethrough in the horizontal direction and a second passageway configured to permit the tether to pass therethrough in the vertical direction;
a threaded aperture extending through the upper surface and into a common space of the first passageway and the second passageway; and
an immobilization assembly including a set screw and a wedge, the set screw being disposed within the threaded aperture, wherein the set screw includes a conical tip configured to directly contact a conically shaped surface of the wedge;
wherein the immobilization assembly is configured to be rotated from an open position in which the tether is permitted to pass through the first passageway to a closed position in which the tether is immobilized within the common space, and
wherein in the closed position, the wedge is configured to pin the tether against a bearing surface of the common space.

18. The multiaxial receiver of claim 17, wherein:
in operation from the open position to the closed position the set screw is configured to translate in the vertical direction such that, in turn, the wedge is translated in the horizontal direction.

* * * * *